US011911330B2

(12) United States Patent
Deshpande et al.

(10) Patent No.: US 11,911,330 B2
(45) Date of Patent: *Feb. 27, 2024

(54) UPPER-BODY ROBOTIC EXOSKELETON

(71) Applicant: Board of Regents, The University of Texas System, Austin, TX (US)

(72) Inventors: Ashish Warren Deshpande, Austin, TX (US); Bongsu Kim, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/346,392

(22) Filed: Jun. 14, 2021

(65) Prior Publication Data

US 2021/0298983 A1 Sep. 30, 2021

Related U.S. Application Data

(60) Continuation of application No. 16/581,028, filed on Sep. 24, 2019, now Pat. No. 11,033,449, which is a
(Continued)

(51) Int. Cl.
*A61H 1/02* (2006.01)
*B25J 9/00* (2006.01)
(Continued)

(52) U.S. Cl.
CPC .................. *A61H 1/02* (2013.01); *A61F 2/54* (2013.01); *A61F 2/76* (2013.01); *A61F 2/78* (2013.01);
(Continued)

(58) Field of Classification Search
CPC ...... A61H 1/02; A61H 1/0274; A61H 1/0277; A61H 1/0281; A61H 2201/1207; A61H 2201/1215; A61H 2201/1614; A61H 2201/1616; A61H 2201/1619; A61H 2201/1621; A61H 2201/1623; A61H 2201/1626; A61H 2201/1638; A61H 2201/165; A61H 2201/1671;
(Continued)

(56) References Cited

U.S. PATENT DOCUMENTS 4,800,897 A 1/1989 Nilsson
5,282,460 A * 2/1994 Boldt ....................... B25J 9/146
403/119

(Continued)

OTHER PUBLICATIONS

International Searching Authority, International Search Report and Written Opinion dated Aug. 25, 2015 in PCT Patent Application No. PCT/US2014/058326 (15 pages).
(Continued)

*Primary Examiner* — Justine R Yu
*Assistant Examiner* — Matthew R Moon
(74) *Attorney, Agent, or Firm* — Trop, Pruner & Hu, P.C.

(57) ABSTRACT

A robotic exoskeleton including a back portion providing at least two degrees of freedom, two shoulder portions, each shoulder portion providing at least five degrees of freedom, two elbow portions, each elbow portion providing at least one degree of freedom, and two forearm portions, each forearm portion providing at least one degree of freedom.

10 Claims, 19 Drawing Sheets

Related U.S. Application Data division of application No. 15/082,783, filed on Mar. 28, 2016, now Pat. No. 10,463,560, which is a continuation of application No. PCT/US2014/058326, filed on Sep. 30, 2014.

(60) Provisional application No. 61/884,593, filed on Sep. 30, 2013.

(51) Int. Cl.
  *A61F 2/54* (2006.01)
  *A61F 2/76* (2006.01)
  *A61F 2/78* (2006.01)

(52) U.S. Cl.
  CPC ......... *A61H 1/0274* (2013.01); *A61H 1/0277* (2013.01); *A61H 1/0281* (2013.01); *B25J 9/0006* (2013.01); *A61H 2201/1207* (2013.01); *A61H 2201/1215* (2013.01); *A61H 2201/1454* (2013.01); *A61H 2201/1481* (2013.01); *A61H 2201/165* (2013.01); *A61H 2201/1614* (2013.01); *A61H 2201/1616* (2013.01); *A61H 2201/1619* (2013.01); *A61H 2201/1621* (2013.01); *A61H 2201/1638* (2013.01); *A61H 2201/1676* (2013.01); *A61H 2201/5058* (2013.01); *A61H 2201/5061* (2013.01); *A61H 2201/5064* (2013.01); *A61H 2201/5069* (2013.01)

(58) Field of Classification Search
  CPC .... A61H 2201/1676; A61H 2201/5069; A61H 1/00; A61H 1/0107; A61H 2201/12; A61H 2201/16; A61H 2201/1673; A61H 2201/50; A61H 2201/5007; A61H 2201/5061; A61H 2201/5064; A61H 2201/5092; A61F 2/54; A61F 2/76; A61F 2/78; B25J 9/0006
  See application file for complete search history.

(56) References Cited

U.S. PATENT DOCUMENTS

| | | | |
|---|---|---|---|
| 6,155,993 | A | 12/2000 | Scott |
| 6,301,526 | B1 | 10/2001 | Kim et al. |
| 6,450,757 | B1 * | 9/2002 | Saeki ............... H01L 21/687 |
| | | | 414/744.5 |
| 6,558,107 | B1 | 5/2003 | Okuno |
| 9,592,174 | B2 | 3/2017 | Hong et al. |
| 2003/0115954 | A1 | 6/2003 | Zemlyakov et al. |
| 2006/0150753 | A1 | 7/2006 | Massimo et al. |
| 2007/0225620 | A1 | 9/2007 | Carignan et al. |
| 2008/0009771 | A1 | 1/2008 | Perry et al. |
| 2010/0016766 | A1 | 1/2010 | Zhang et al. |
| 2010/0204804 | A1 | 8/2010 | Garrec |
| 2011/0251533 | A1 * | 10/2011 | Han ............... A63B 23/1245 |
| | | | 601/33 |
| 2012/0172769 | A1 | 7/2012 | Garrec |
| 2013/0060171 | A1 * | 3/2013 | Fu .................. A61H 1/00 |
| | | | 601/5 |
| 2013/0158438 | A1 | 6/2013 | Scott et al. |
| 2013/0237883 | A1 | 9/2013 | Malosio et al. |

OTHER PUBLICATIONS

International Searching Authority, International Preliminary Report on Patentability dated Apr. 14, 2016 in PCT Patent Application No. PCT/US2014/058326 (10 pages).

* cited by examiner

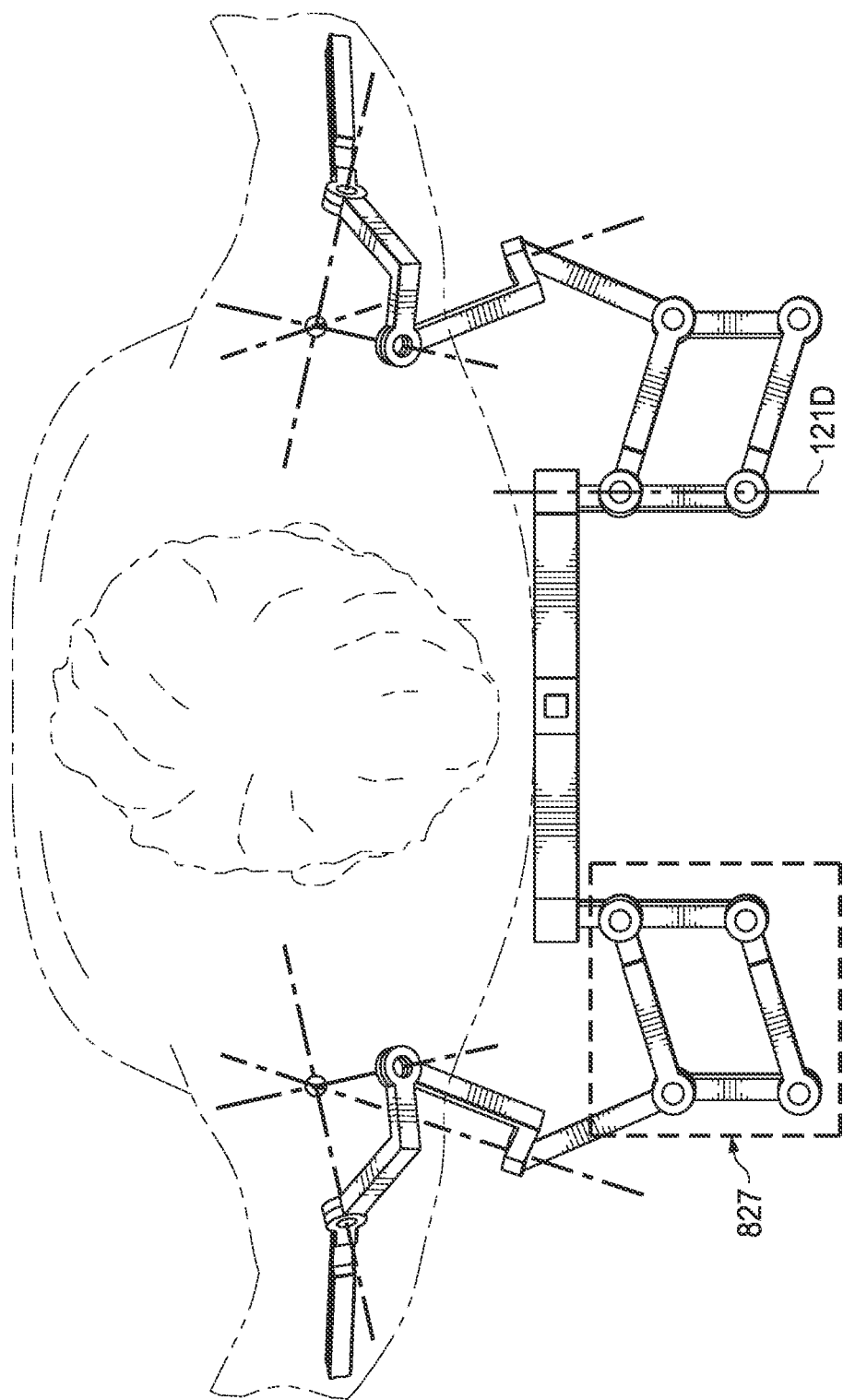

UPPER-BODY ROBOTIC EXOSKELETON

CROSS-REFERENCE TO RELATED APPLICATION

This application is a continuation of U.S. patent application Ser. No. 16/581,028, filed Sep. 24, 2019, which is a divisional of U.S. patent application Ser. No. 15/082,783, filed Mar. 28, 2016, now U.S. Pat. No. 10,463,560, granted Nov. 5, 2019, which is a continuation application of PCT Application Number PCT/US2014/058326 filed Sep. 30, 2014, and entitled "Upper-Body Robotic Exoskeleton", which claims the benefit of U.S. Provisional Application No. 61/884,593 filed Sep. 30, 2013, and entitled "Upper-Body Robotic Exoskeleton". The content of each of the above applications is hereby incorporated by reference.

STATEMENT OF GOVERNMENT INTEREST

This invention was made with government support under Grant no. ECCS1157907 awarded by the National Science Foundation. The government has certain rights in the invention.

TECHNICAL FIELD OF THE DISCLOSURE

This disclosure relates generally to biomechanics and robotics, and in particular, to an upper-body robotic exoskeleton.

BACKGROUND

Exoskeletons are mechatronic systems worn by a person in such a way that a direct transfer of mechanical power from the exoskeleton occurs. These robotic mechanisms have been applied in a variety of settings, for example, telemanipulation, man-amplification, rehabilitation, and to assist impaired human motor control. However, many of these applications of exoskeleton devices have yet to find widespread use, acceptance, or practicality.

One example area in which these devices have been proposed is the treatment of stroke. Stroke affects thousands of Americans every year and the recovery process is long, difficult, and costly. The use of an upper-body robotic exoskeleton may potentially reduce the length, difficulty, and cost of this recovery process.

Various efforts have been proposed to provide a robotic exoskeleton for the upper-body. However, there still exists a need in the art for improvements in this field.

SUMMARY

In one embodiment, the present disclosure may include a robotic shoulder joint comprising a first hinge joint with a first axis of rotation oriented towards a center of a human shoulder joint and a second hinge joint coupled to the first hinge joint, with a second axis of rotation oriented between approximately 55° and 75° from the first axis of rotation and oriented towards the center of the human shoulder joint. The robotic shoulder joint also comprises a third hinge joint coupled to the second hinge joint, with a third axis of rotation oriented between approximately 55° and 75° from the second axis of rotation and oriented between approximately 50° and 80° from the first axis of rotation, and oriented towards the center of the human shoulder joint, the third hinge joint acting with the first hinge joint and the second hinge joint to replicate a ball and socket joint. The robotic shoulder joint additionally comprises a fourth hinge joint coupled to the third hinge joint with a fourth axis of rotation to provide a fourth degree of freedom and oriented to replicate horizontal motion of the clavicle, where the fourth hinge joint is a parallelogram linkage and a fifth hinge joint coupled to the fourth hinge joint with a fifth axis of rotation to provide a fifth degree of freedom and oriented to replicate vertical motion of a clavicle.

In an alternative embodiment, the present disclosure may include a robotic exoskeleton comprising a back portion providing at least two degrees of freedom, two shoulder portions, each shoulder portion providing at least five degrees of freedom, two elbow portions, each elbow portion providing at least one degree of freedom, and two forearm portions, each forearm portion providing at least one degree of freedom.

In an additional embodiment, the present disclosure may include a robotic forearm joint comprising a first hinge joint with a first axis of rotation outside of a human forearm, a grounded linkage coupled to the first hinge joint, a second linkage coupled to the first grounded linkage via the first hinge joint and coupled to a third linkage via a second hinge joint, a fourth linkage coupled to the third linkage via a third hinge joint and coupled to the grounded linkage via a fourth hinge joint, a first pulley coupled to the second linkage, and a second pulley coupled to the third linkage. The second linkage and the fourth linkage rotate with respect to the grounded linkage and translate the third linkage along a first curvature radius, and the second pulley revolves around a center of revolution with the first curvature radius, the center of revolution located inside of a human forearm. The first and second pulleys are connected by a transmission such that as the second pulley revolves around the center of revolution, the second pulley simultaneously rotates about a center point of the second pulley such that a same face of the forearm portion faces the human forearm as the second pulley revolves around the second axis of rotation.

BRIEF DESCRIPTION OF THE DRAWINGS

For a more complete understanding of the present disclosure and its features and advantages, reference is now made to the following description, taken in conjunction with the accompanying drawings, in which:

FIGS. 8A-8E illustrate an example of an alternative upper-body device, in accordance with the present disclosure;

DETAILED DESCRIPTION

The present disclosure relates to an upper-body robotic exoskeleton. A first joint or set of joints may replicate the motion of the back, a second set of joints may replicate the motion of the shoulder, a third joint may replicate the motion of the elbow, and a fourth joint or set of joints may replicate the motion of the forearm. The second set of joints replicating the motion of the shoulder may include five degrees of freedom. The second set of joints may include three degrees of freedom that may replicate the three-dimensional motion of the arm at the end of the shoulder, or in other words, may replicate a ball and socket joint (the glenohumeral joint) in the shoulder. The second set of joints may also include two degrees of freedom that may replicate the shoulder girdle motion of protraction/retraction and elevation/depression, or in other words may revolve the ball and socket joint in the shoulder vertically and forward/backward. The fourth joint or set of joints may include an arrangement of a parallelogram to allow the axis of the revolution of the ball and socket joint to be along the center of rotation for the protraction and retraction of the shoulder girdle, replicating rotation of the clavicle from outside the shoulder.

Figure 1A:
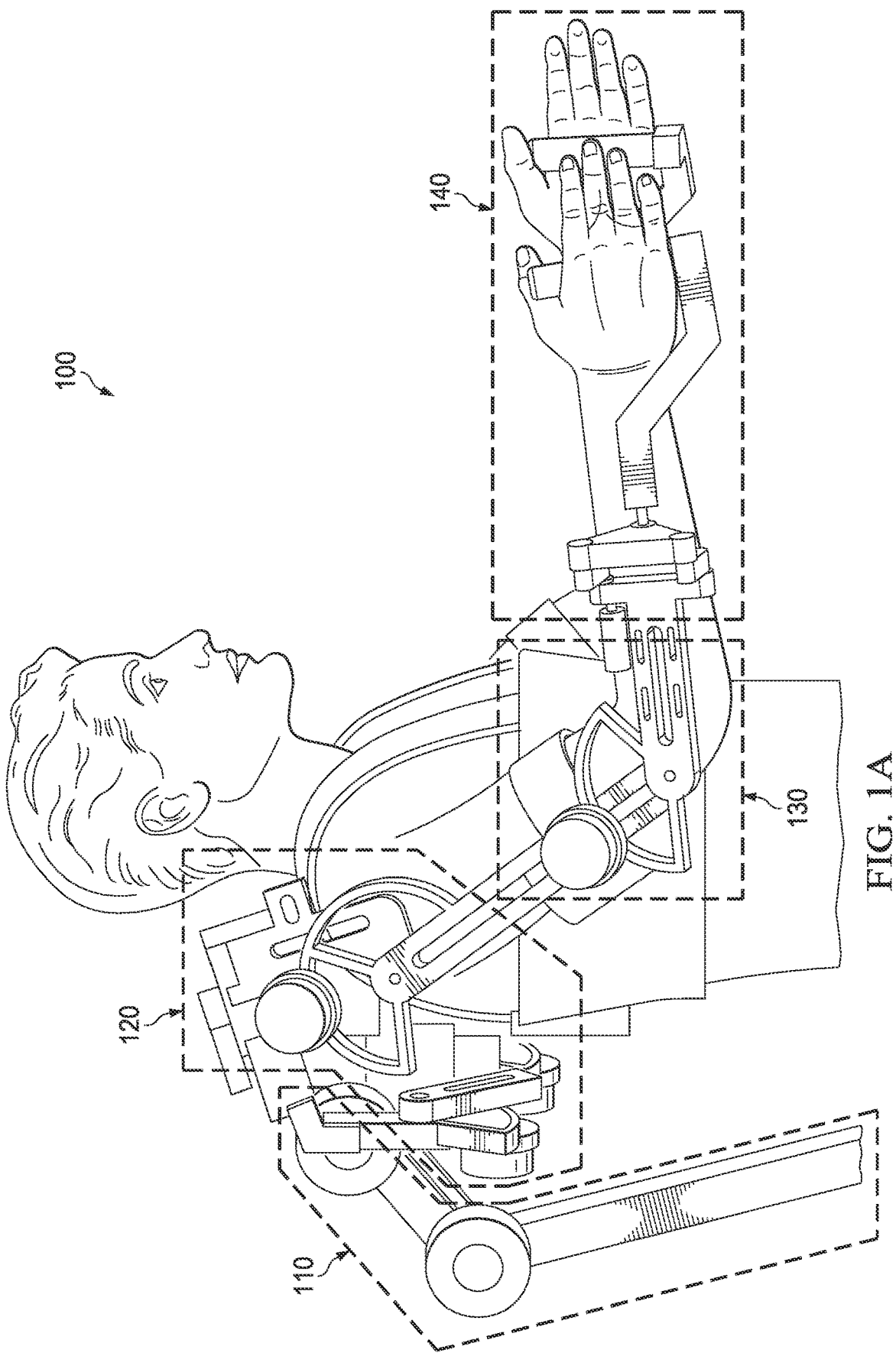
FIGS. 1A-1D illustrate an example embodiment of an upper-body device, in accordance with the present disclosure.
Figure 1B:
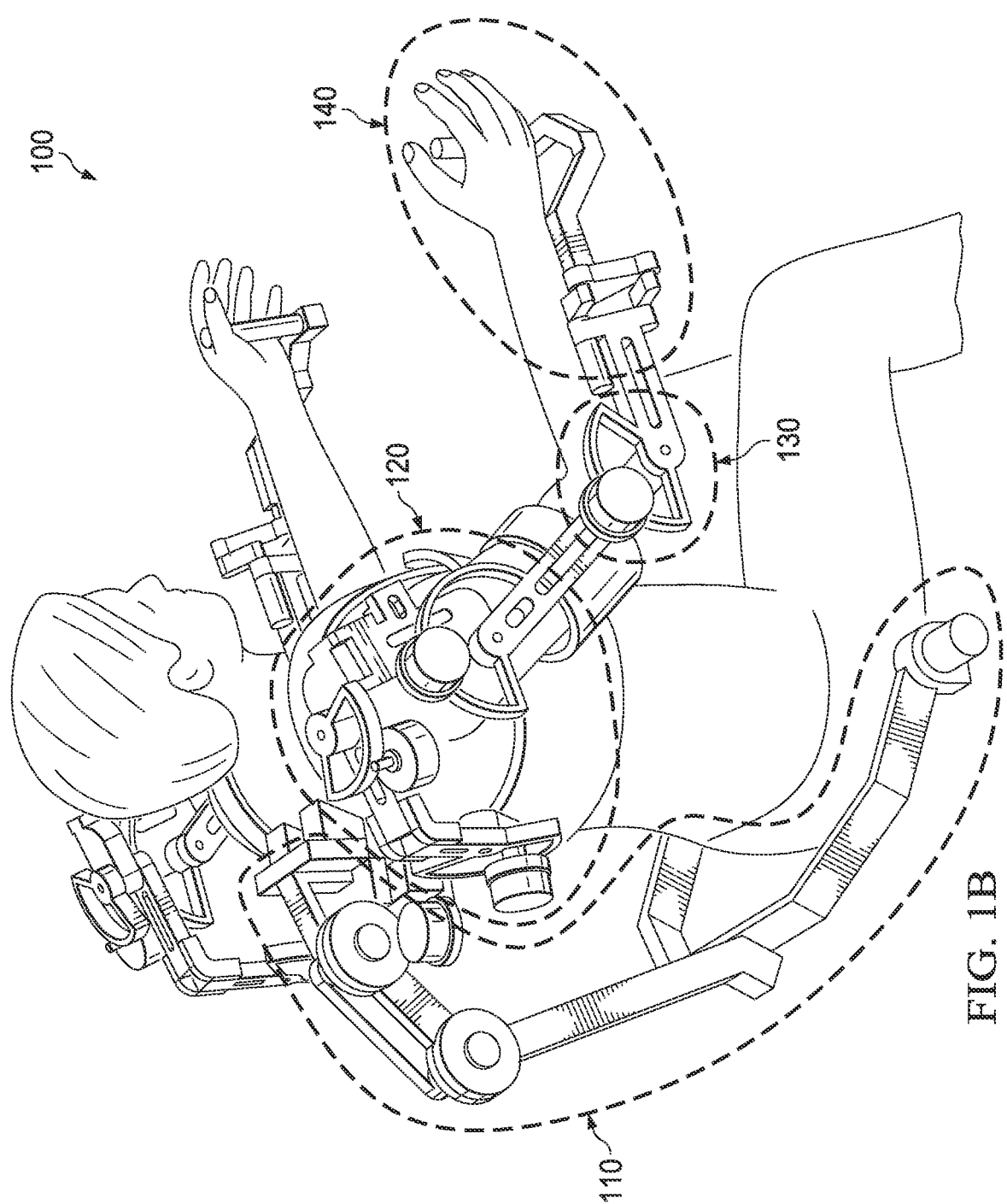
Figure 1C:
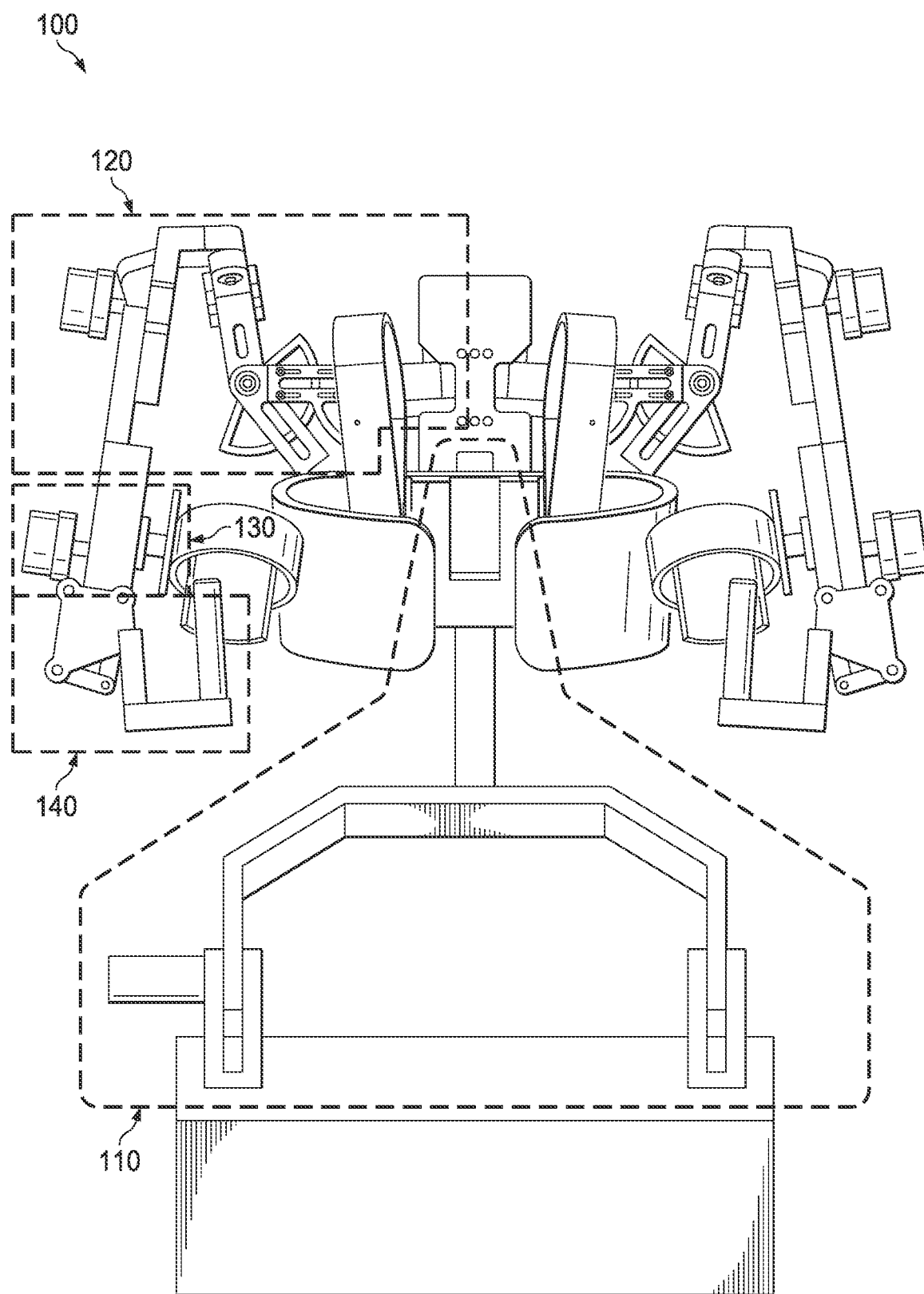
Figure 1D:
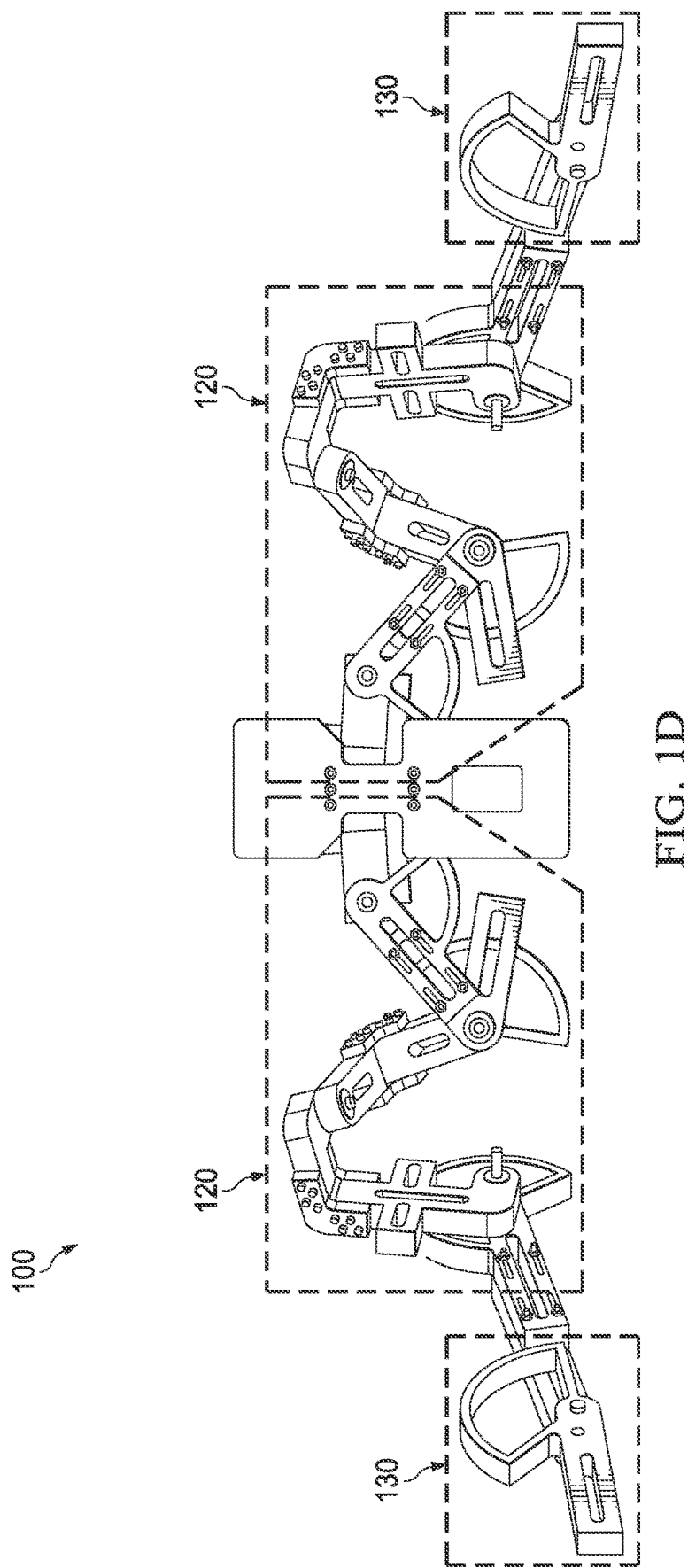

FIGS. 1A-1D illustrate an example of an upper-body device, in accordance with the present disclosure. For example, FIG. 1A illustrates an upper-body device 100. Upper body device 100 may be an upper-body robotic exoskeleton that may include a back portion 110, a shoulder portion 120, an elbow portion 130, and a forearm portion 140. FIG. 1A illustrates a side view of upper-body device 100 with an individual using the device. FIG. 1B illustrates a perspective view of upper-body device 100 with an individual using the device. FIG. 1C illustrates a front view of upper-body device 100 without an individual using the device. FIG. 1D illustrates a front view of upper-body device 100 without an individual or a harness for an individual using the device.

As shown in FIG. 1D, various portions of the framework of upper-body device 100 may be adjustably sized such that portions of the framework may be shortened or lengthened depending on the size and physiology of the user of upper-body device 100. For example, various slots in members of the framework of upper-body device 100 may be used with screws, nuts, bolts, tabs, or other connecting members within the slots to connect two slidably engaged members of the framework of upper-body device 100. If a different size is desired, the screw, nut bolt, tab or other connecting member may be loosened and the two slidably engaged members may be slid past each other. Once a desired size is reached, the screw, nut bolt, tab, or other connecting member within the slot may be retightened. This may allow for a customizable framework for upper-body device 100 which may be easily and rapidly re-sized based on the user of upper-body device 100. A single slot may be used, allowing two dimensions of adjustability, or two or more parallel slots may be used, allowing only one dimension of adjustability. As used herein, the term "framework" may refer to structural members of upper-body device 100, including both non-moving and moving (e.g. a joint) portions of upper-body device 100. It will be appreciated that other adjustable systems may be used to change the sizes of various portions of the framework of upper-body device 100, and that the use of slots is merely an illustrative example.

Figure 2:
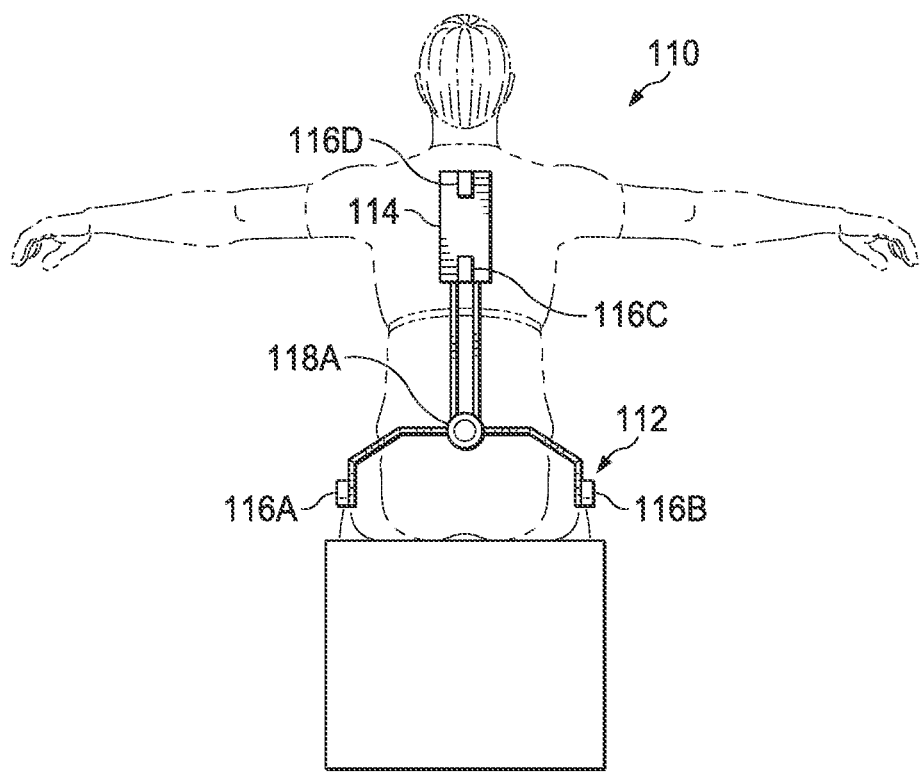
FIG. 2 illustrates an example of a back portion of an upper-body device, in accordance with the present disclosure.
Figure 2A:
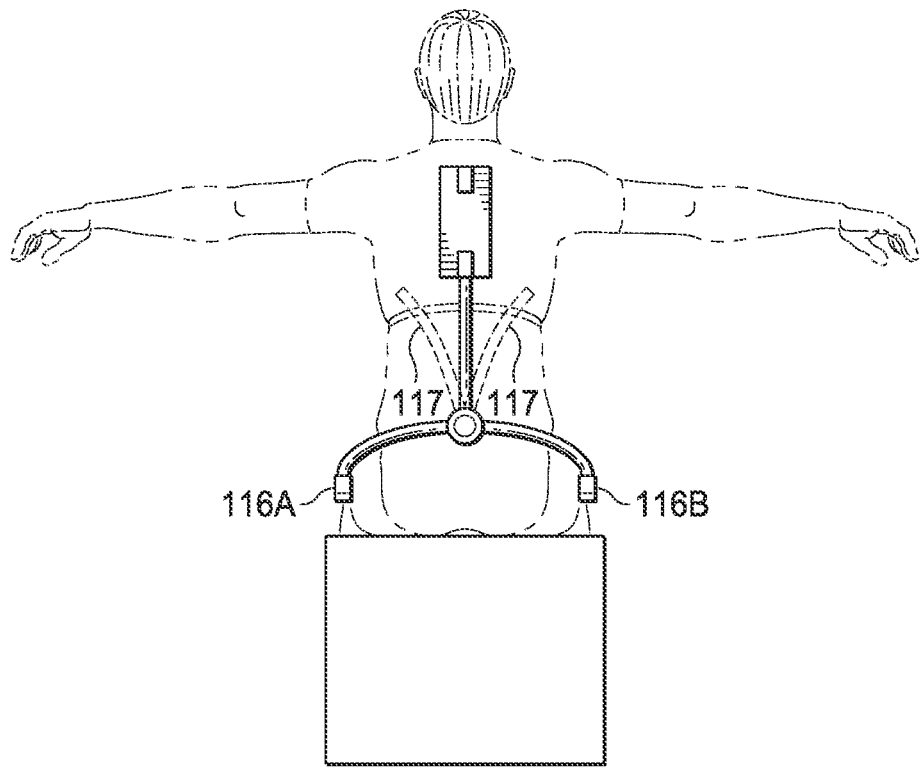
FIG. 2A illustrates an alternative example of a back portion of an upper-body device; in accordance with the present disclosure.

FIG. 2A illustrates one embodiment of back portion 110. For example, as shown in FIG. 2A, back portion 110 may include a first back joint 116A and/or 116B. First back joint 116 may provide a first degree of freedom, for example, replicating a user of upper-body device 100 rocking forward and backward. This may replicate part of the forward/backward motion of the waist coming from the hip joint. First back joint 116A and/or 116B may be aligned to a line which connects both hip joints along the frontal plane. This may replicate anatomical motion where the forward and backward motion of the upper body may have a first pivot point at the hip joint, and then additional curvature from the spinal column adding a leaning motion. Joint 116A and 116B may have a single motor on only one side, or may provide a second motor at joint 116B so as to provide supportive motion or torque to replicate the waist's flexion and extension (i.e. the forward and backward motion). Back portion 110 may also include a second back joint or set of joints 114. Second back joint 114 may provide one or more additional degrees of freedom, for example, replicating the forward and backward motion of a user of upper body device 100. Back portion 110 may also include a third degree of freedom, or set of joints 118A. This may replicate the lateral flexion motion of the upper body. The twist motion of the spinal column of a user may also have an axis of rotation inside the upper body approximately parallel to a person's spinal column. To replicate the motion about this axis, a larger version of a parallelogram mechanism (for example, that shown in FIG. 6) may be implemented around the waist rim or the column 117 (as shown in FIG. 2B). In this way back portion may have complete supportive motion around the waist and spinal column of a user. However, the inclusion of such a parallelogram linkage and other joints may increase complexity of back portion 110.

As will be appreciated, the spinal column includes a large number of individual vertebrae, creating a large number of movement points in the back. With only a single degree of freedom at second back joint 114, the entire range of motion possible by a spinal column may not be completely replicated. Additional joints may be added, however, with additional degrees of freedom, additional motors 116C and 116D and thus, additional weight and complexity may be added. Thus, there may be a design trade-off between weight/complexity and more human-like motion as the number of degrees of freedom is varied at second back joint 114. An adequate number of joints (i.e. degrees of freedom) for second back joint 114 may be selected based on the application in which upper body device 100 may be used. For example, if the weight of motors 116C and 116D is not a concern and complete motion of the entire curvature of the back is important, second back joint 114 may comprise a larger number of degrees of freedom. If the weight of motors 116C and 116D is a concern and a simple replication of the spinal column is appropriate, second back joint 114 may comprise a smaller number of degrees of freedom, for example, only one or two degrees of freedom to replicate the forward and backward motion of a user of upper-body device 100.

By having only one revolute joint of 116 as shown in FIG. 2, the large portion of the forward and backward motion of the waist can be supported by actuators at joints 116A or 116B. As shown in FIG. 2B, other motion such as lateral flexion and twist motion of the spinal column may be replicated by a flexible column 117 passively (for example, without having motors attached to replicate motion). Flexible column 117 may be made of any suitable material, such as a carbon fiber tube. Allowing some range of motion for the side to side or twist motion passively, the flexible column may support the upper body. In this way, complexity of the back supporter may be mitigated.

In some embodiments, back portion 110 may include three degrees of freedom, including joints 116A and/or 116B, For example, as shown in FIG. 2A, second joint 114 may provide two degrees of freedom, with motors 116C and 116D each operating one of the two degrees of freedom. As will be appreciated, back portion 110 may be built using adjustably-sizable framework.

Figure 3:
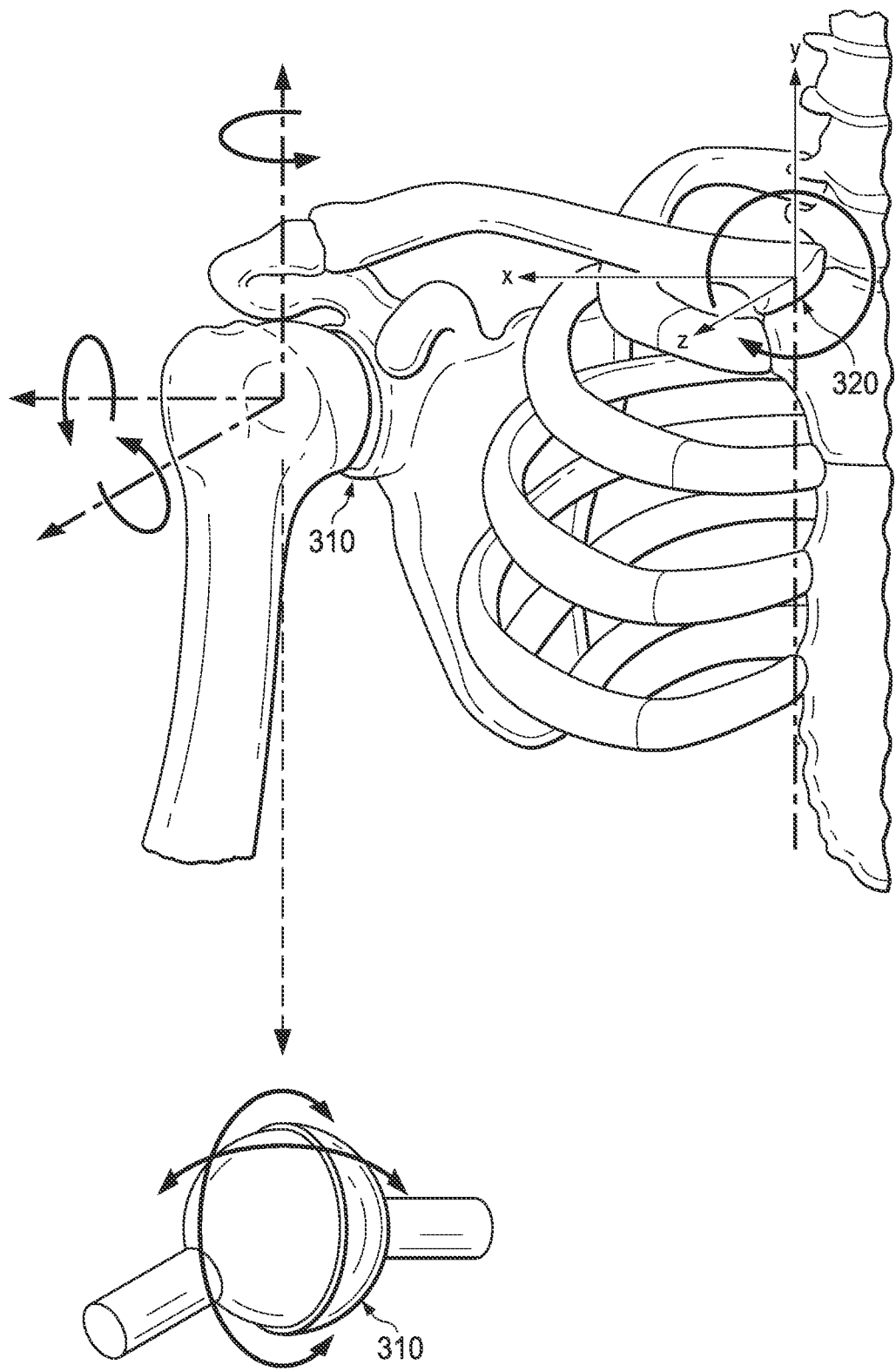
FIG. 3 illustrates an example of human shoulder joint motion, in accordance with the present disclosure.

FIG. 3 illustrates an example of human shoulder joint motion. For example, as shown in FIG. 3, a human shoulder joint may include a glenohumeral joint 310 and a sternoclavicular joint 320. Glenohumeral joint 310 may allow three degrees of freedom of the arm about the shoulder joint. However, because of tissue and interference, glenohumeral joint 310 may not provide 360° of motion, instead, allowing a smaller range of motion. For example, the arm cannot bend all the way flat across the back without damaging the shoulder joint. This motion may be represented by a ball and socket joint with three axes of rotation with a center point in the middle of the ball of ball and socket joint 310.

The scapula and clavicle form the shoulder girdle upon which the socket part of the ball and socket joint sits. The only bony connection of the shoulder girdle to the thorax is through the sternoclavicular joint. Therefore, the shoulder girdle motion may be represented by the motion in sternoclavicular joint 320 that may provide motion that moves the entire ball and socket joint 310. For example, sternoclavicular joint 320 may allow the shrugging motion of the shoulder joint (e.g., shoulder protraction and retraction), or vertical motion of ball and socket joint 310 (e.g., shoulder elevation and depression). While this motion may be described as vertical, it will be appreciated that it may be more accurately described as a rotation of ball and socket joint 310 about the center point of sternoclavicular joint 320 about the z-axis, rather than completely vertical motion. Sternoclavicular joint 320 may also allow for the forward and backward motion of ball and socket joint 310. While this motion may be described as forward and backward, it will be appreciated that the motion may more accurately be described as a rotation about the center point of sternoclavicular joint 320 about the y-axis. However, the actual center of rotation in the shoulder girdle motion may shift away from sternoclavicular joint 320 due to additional motion in the acromioclavicular joint and constraints from tendons and muscles around sternoclavicular joint 320.

Figure 4:
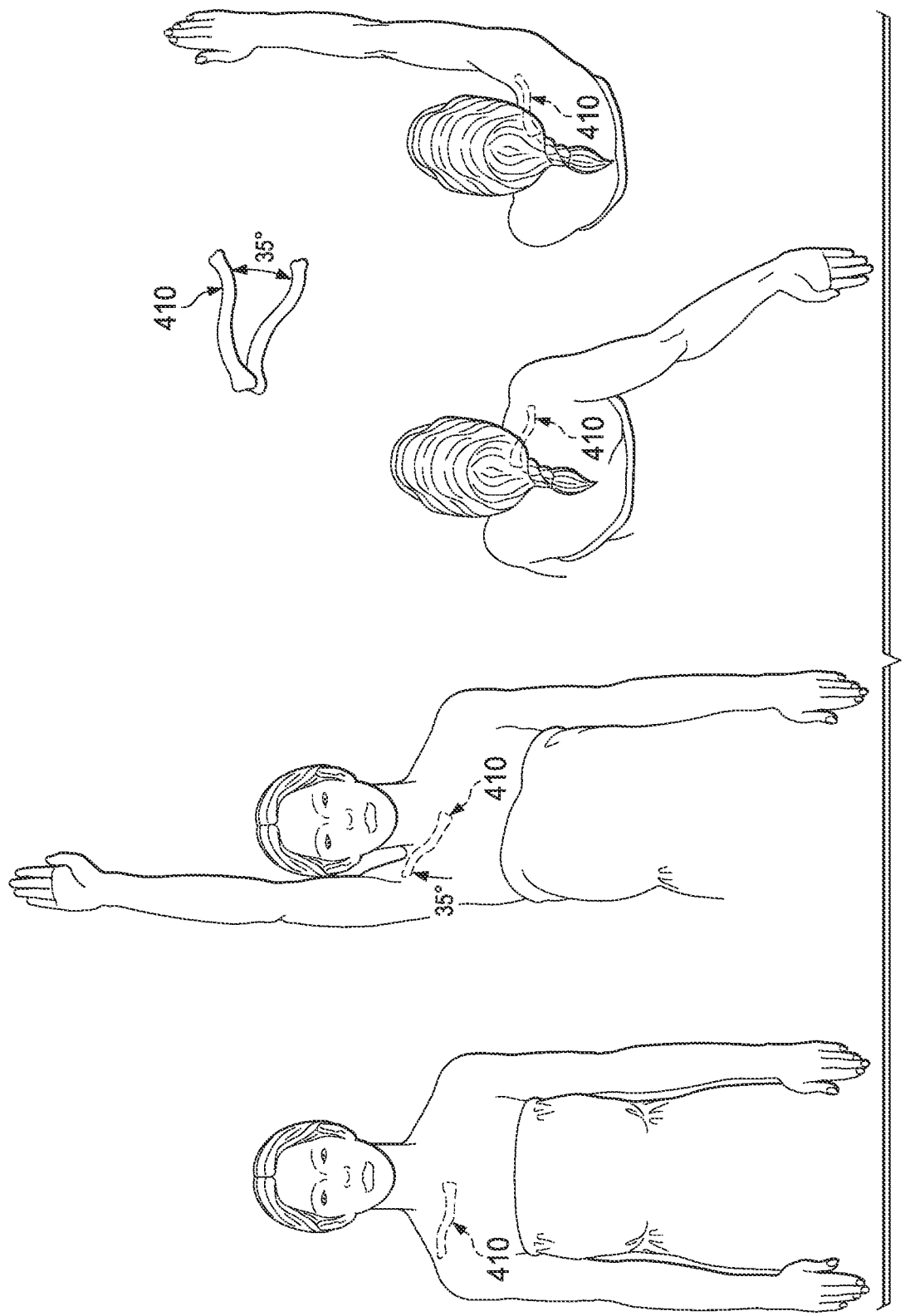
FIG. 4 illustrates an example of clavicle motion, in accordance with the present disclosure.

FIG. 4 illustrates an example of the motion of a clavicle 410, further illustrating the motion of a human shoulder joint. For example, as shown in FIG. 4, when the arm is raised, clavicle 410 may move vertically approximately 35°, or in other words, with reference to FIG. 3, may rotate about the center point of sternoclavicular joint 320 approximately 35° about the z-axis. Additionally, as can be seen in FIG. 4, when reaching forward or backward, clavicle 410 may move forward and backward approximately 35°, or in other words, with reference to FIG. 3, may rotate about the center point of sternoclavicular joint approximately 35° about the y-axis.

Figure 5A:
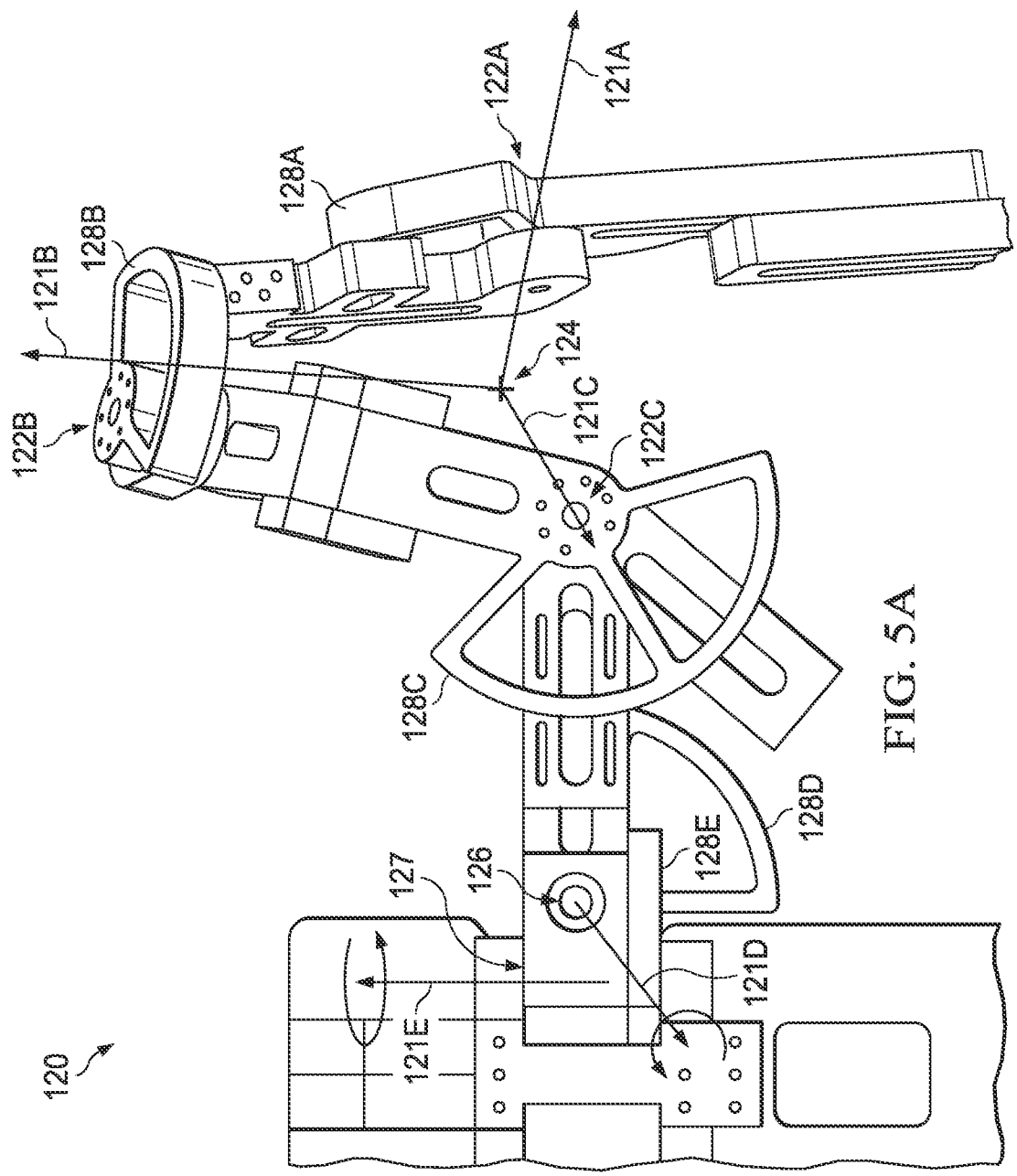
FIGS. 5A and 5B illustrate an example of a shoulder portion of an upper-body device, in accordance with the present disclosure.
Figure 5B:
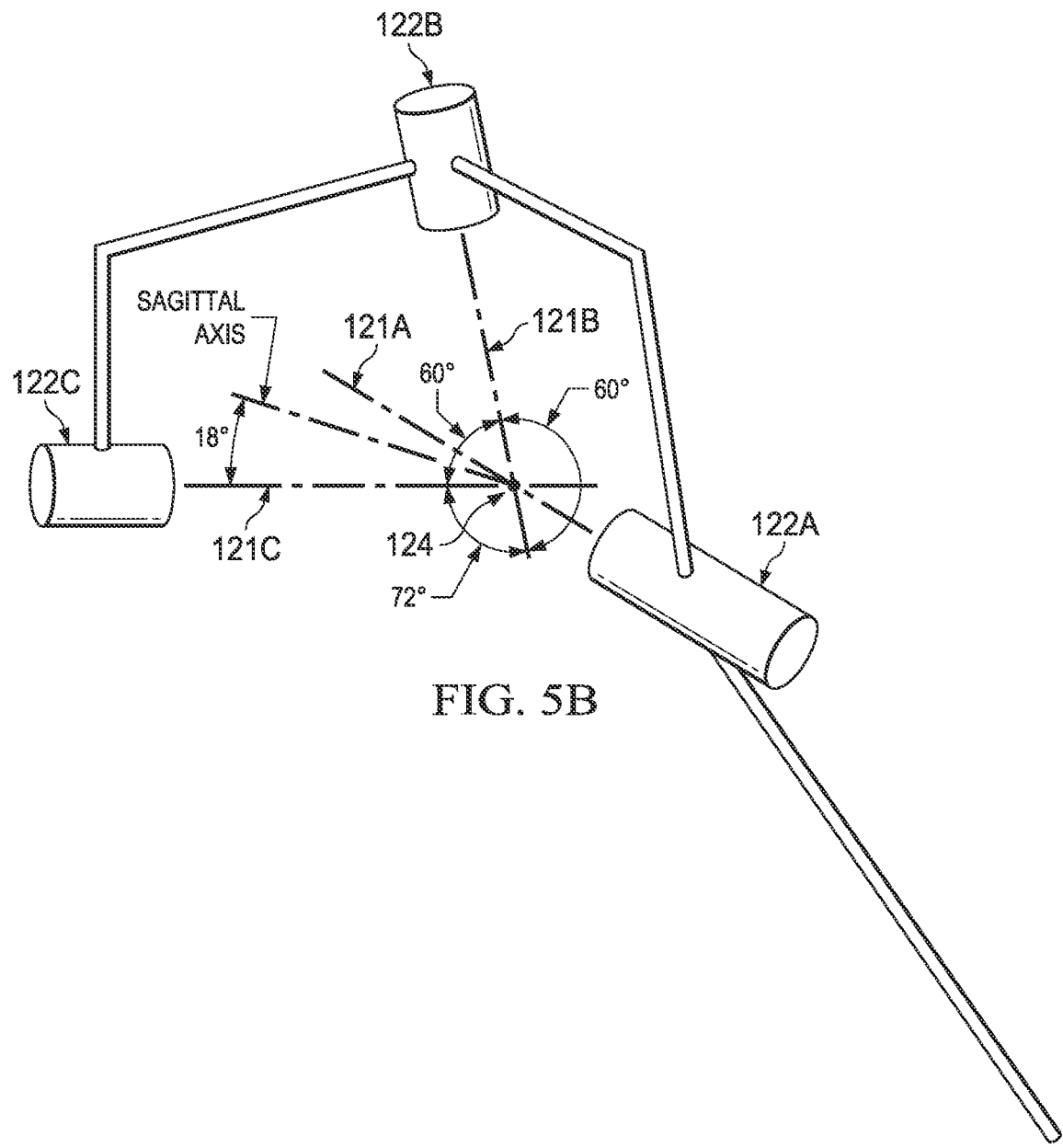

FIGS. 5A and 5B illustrate an example of shoulder portion 120 of upper-body device 100, in accordance with the present disclosure. Shoulder portion 120 of upper-body device 100 may provide five degrees of freedom, or may provide five distinct mechanical hinge joints to represent both ball and socket joint 310 and sternoclavicular joint 320. A first hinge joint 122A may rotate about axis 121A. A second hinge joint 122B may be coupled to first hinge joint 122A. Second hinge joint 122B may rotate about axis 121B. A third hinge joint 122C may be coupled to second hinge joint 122B. Third hinge joint 122C may rotate about axis 121C. The meeting point of axes 121A, 121B, and 121C may be center point 124. The three hinge joints 122A, 122B, and 122C may be oriented such that center point 124 may be located in the center of the ball of ball and socket joint 310 (shown in FIG. 3) of a user of upper body device 100. Thus, the combination of hinge joints 122A, 122B, and 122C may replicate the three degrees of freedom and the motion of ball and socket joint 310. While hinge joints 122A, 122B, and 122C are shown as being connected in that order, another linkage order may be selected. However, this order may be preferable as it may allow the entire framework including motors associated with the hinge joints 122 of upper-body device 100 to remain along the back and along the outside of the arm of a user of upper-body device 100, except for hinge joint 122B, which may be located above a shoulder joint of a user of upper-body device 100. For example, as shown in FIGS. 1A and 1B, nearly the entire framework of upper-body device 100 may be along the back and along the outside of the arm of a user of upper-body device 100.

Figure 9A:
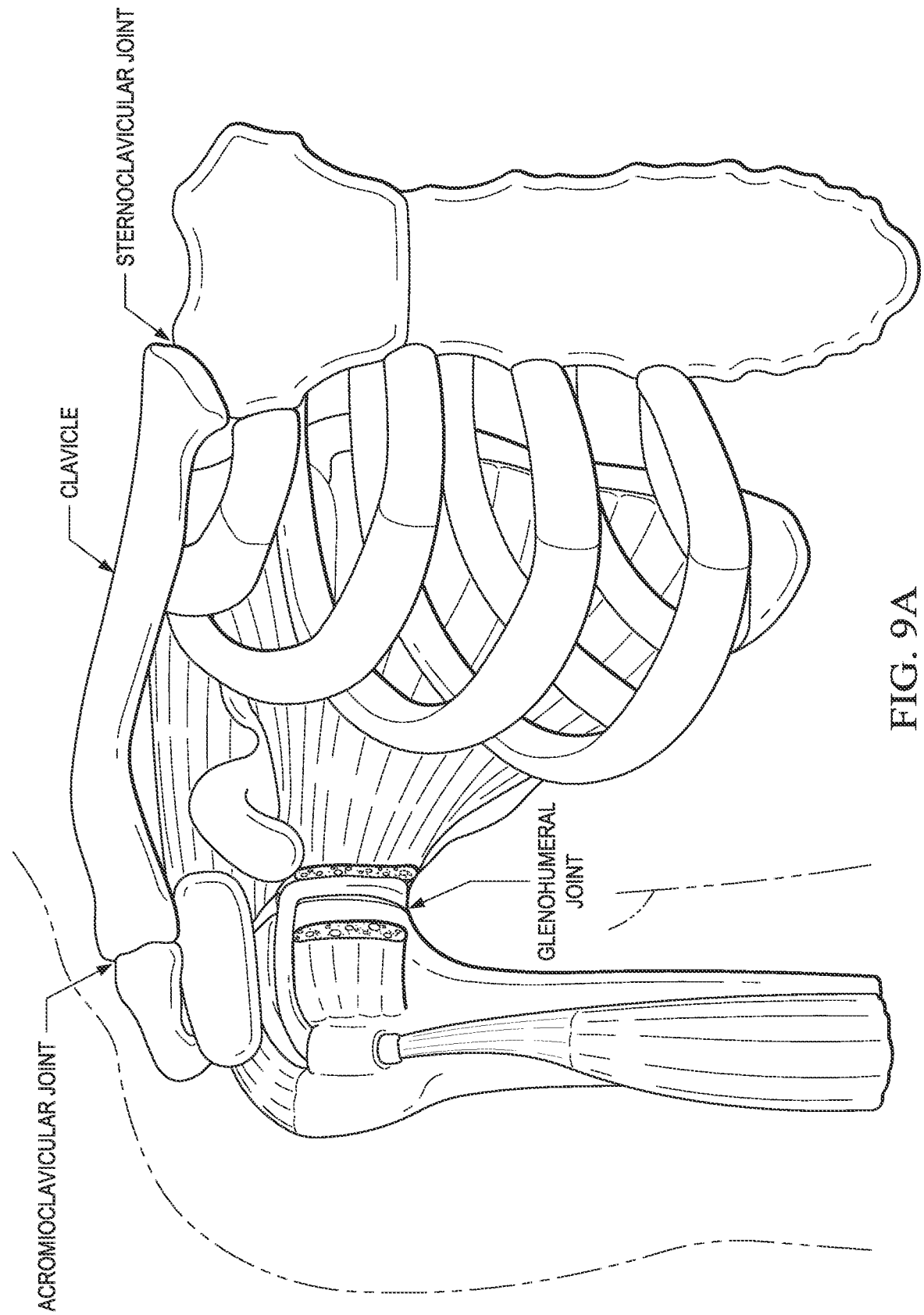
FIGS. 9A and 9B illustrate an example of anatomical features including planes of the body and physiology within the shoulder.
Figure 9B:
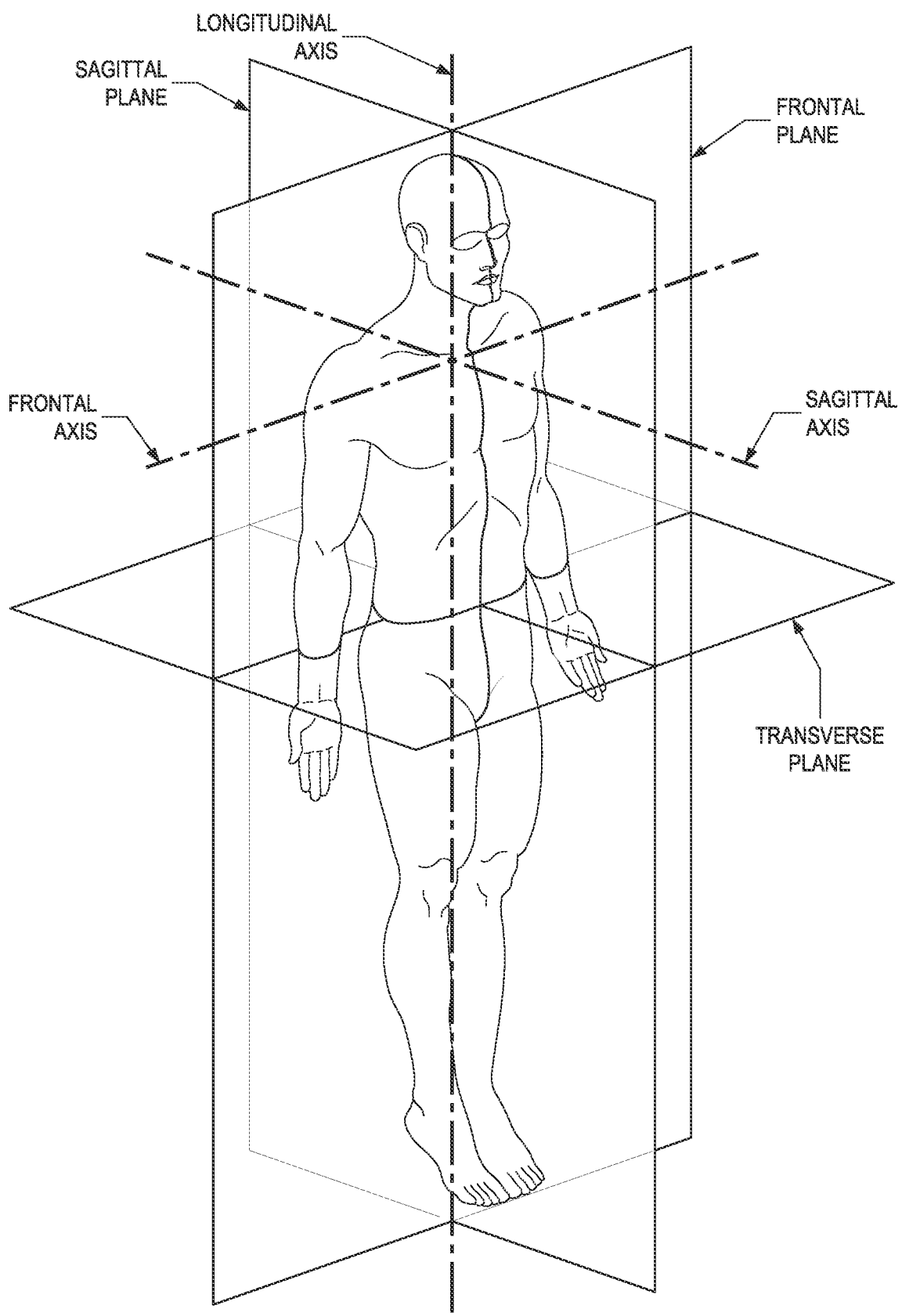

As shown in FIG. 5B, in some embodiments, at the neutral position of a user's shoulder there may be between approximately 50° and 80°, for example approximately 72°, between axis 121A and 121C, and between approximately 55° and approximately 75°, for example approximately 60°, between axis 121A and 121B, and between approximately 55° and approximately 75°, for example approximately 60°, between axis 121B and 122C, where axis 121A may be aligned with the frontal axis of the user, as shown in FIG. 9B. To facilitate this, as shown in simplified form in FIG. 5B, the linkage between hinge joint 122A and 122B may have an oblique angle of between approximately 55° and approximately 75°, for example approximately 60°, and the linkage between hinge joint 122B and 122C may have an oblique angle of between approximately 55° and approximately 75°, for example approximately 60°, and the linkage between hinge joints 122A and 122C may have an oblique angle between approximately 50° and approximately 80°, for example, approximately 72°. While this may limit the effective range of motion of the replicated ball and socket joint, this may still be in line with the range of motion allowed by a typical human shoulder ball and socket joint. In some embodiments, there may be between approximately 50° and approximately 80° between each of hinge joints 122A, 122B, and 122C.

With reference to FIGURE SA, first hinge joint 122A, second hinge joint 122B, and third hinge joint 122C may include an actuator to provide motive force to the movement about axes 121A, 121B, and 121C, respectively. An actuator may be capable of precisely controlling position, speed, and or torque. In one embodiment, hinge joints 122A, 122B, and/or 122C may be coupled to a series elastic actuator composing a serial connection between a spring and a motor with gear reduction. In an alternative embodiment, a geared motor may provide motive force to the movement about each axis via a Capstan drive that may include a set of a large pulley and a small pulley which may be coupled by cable routing.

With reference to FIGURE 5A, shoulder portion 120 of upper-body device 100 may also reproduce at least two degrees of freedom of sternoclavicular joint 320. For example, shoulder portion 120 may include a fourth joint 126, which may rotate about axis 121D. This may reproduce the shoulder elevation/depression that is the vertical motion of sternoclavicular joint 320 or the rotation about the center point of sternoclavicular joint 320 about the z-axis, or in other words, reproduce the shrugging motion of the shoulder. Fourth joint 126 may be coupled to third hinge joint 122C. Shoulder portion 120 may also include a fifth hinge joint 127 which may rotate about axis 121E. This may reproduce the forward and backward motion of sternclavicular joint 320, or the rotation about the center point of sternoclavicular joint 320 about the y-axis, or in other words, reproduce the shoulder protraction/retraction motion of the clavicle. Fifth hinge joint 127 may be coupled to fourth joint 126 and may also be coupled to back portion 110.

Similar to hinge joints 122A, 122B, and 122C, fourth joint 126 and fifth hinge joint 127 may include an actuator to provide motive force to the movement about axis 121D. For example, in one embodiment, joints 126 and 127 may be coupled to a series elastic actuator or a Capstan drive with a geared motor.

As will be appreciated, shoulder portion 120 may be built using adjustably-sizable framework. For example, the distance between fourth joint 126 and third hinge joint 122C may be shortened or lengthened depending on the size of the shoulders of a user of upper-body device 100. Additionally, the distance between hinge joints 122A, 122B, and 122C may be lengthened or shortened depending on the thickness of the shoulders of the user of upper-body device 100.

With reference to FIG. 1D, elbow portion 130 may include a single hinge joint with an axis of rotation perpendicular to the arm of a user of upper-body device 100 such that the bending motion of the elbow may be reproduced. The framework between shoulder portion 120 and elbow portion 130 and between elbow portion 130 and forearm portion 140 may be adjustable depending on the arm-length of the user of upper-body device 100.

Figure 6:
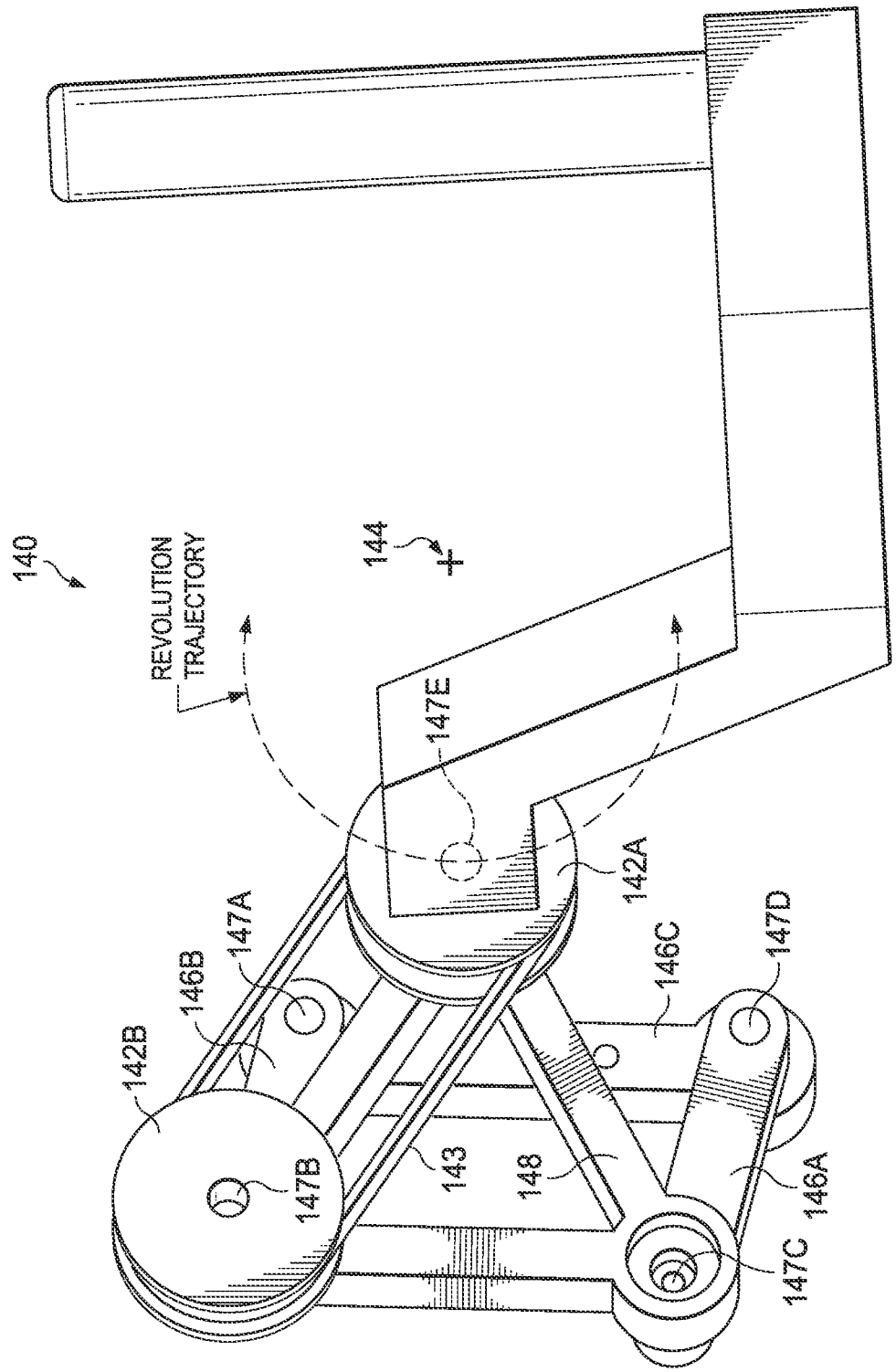
FIG. 6 illustrates an example of a forearm portion of an upper-body device, in accordance with the present disclosure.

FIG. 6 illustrates an example of forearm portion 140 of upper-body device 100, in accordance with the present disclosure. As shown in FIG. 6, forearm portion 140 may include a center point 144 with an axis of rotation. The axis of rotation may pass through approximately the middle of the forearm of a user of upper-body device 100. However, this may pose difficulties in generating the desired rotation as the forearm occupies the space in which the pivot point resides.

In one embodiment, to achieve the desired rotation, a four-bar parallelogram linkage may be used. This may facilitate the transfer of the location of the axis of rotation for a given motion. For example, when arm 146C is fixed and if a rotational force were applied at 147B with respect to the linkage 148, and that point were fixed, point 147B would revolve along a circular path with radius equal to that of arm 146B of the parallelogram and about the axis through point 147A. In like manner, if arm 146C of the parallelogram were fixed, point 147C would rotate along a circular path with radius equal to the length of arm 146A about the axis through point 147D. This would effectively transfer the location of the axis of rotation from point 147A to point 147D for the motion at point 147C. A linkage 148 may be used to connect points 147B and 147C to point 147E. Because of a rigid linkage 148, the rotational motion about the axis through point 147A may also be transferred such that point 147E revolves along a circular path about an axis through point 144, while the distance from point 147E to point 144 would be equal to the arm length of arms 146A and 146B. Center of revolution 144 may be shifted from the point 147A by a distance and a direction from the point 147B to the point 147E.

This parallelogram linkage may thus effectively move the axis of rotation from point 147A, where a force may be applied, to point 144. In addition to the relocation of the axis of rotation, transmission 143, such as a belt, a gear train, or an auxiliary parallelogram, may be used to couple pulleys 142A and 142B. In this way, as pulley 142B revolves about point 147A, it may also cause pulley 142A to rotate about point 147E. In such an embodiment, pulley 142A thus experiences two distinct motions. First, pulley 142A revolves about point 144, and second, pulley 142A also rotates about point 147E. This may effectively keep the same face of forearm portion 140 facing the arm of a user of upper-body device 100, similar to the phenomenon seen as the moon rotates on its own axis while also orbiting the earth such that the same view of the moon always faces the earth. Pulley 142B may be coupled to arm 146B such that pulley 142B rotates together with arm 146B. In embodiments where pulley 147A and arm 146B rotate in the same direction with a one-to-one speed ratio, other mechanism may be implemented, such as a gear train or an auxiliary parallelogram linkage.

As will be appreciated, forearm portion 140 may be built using adjustably-sizable framework. For example, arm 146A and 146B may be modified to change the radius of curvature for the rotation, depending on the size of the user of upper-body device 100. Additionally, linkage 148 may be modified in size to modify the location of point 144 to better accommodate the axis of rotation of the forearm of the user of upper-body device 100.

In an alternative embodiment, a circular track could be used around the forearm of a user of upper-body device 100. However, this may introduce increased bulk and may require a distinct track to be created for each sized device. Thus, the embodiment utilizing the parallelogram linkage described above may be preferable.

Figure 7:
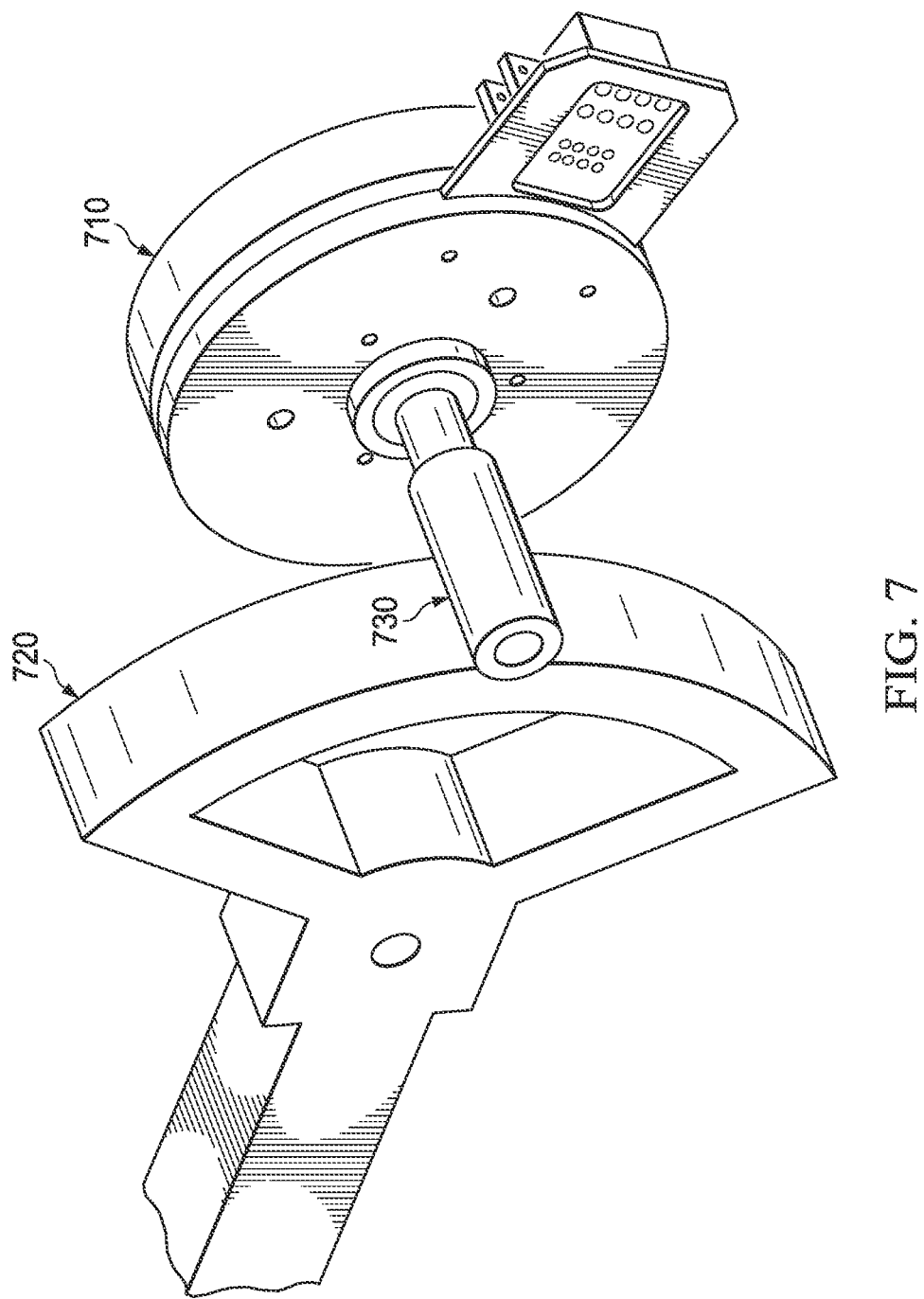
FIG. 7 illustrates an example of a motor, in accordance with the present disclosure.

FIG. 7 illustrates an example of a motor, in accordance with the present disclosure. For any given motor 710, it may have a fixed total power (P). This may be the product of torque ($\tau$) and angular velocity ($\omega$), or $P=\tau \cdot \omega$. In some embodiments, each of the degrees of freedom of each of the joints may have an independent motor 710 providing the force for that particular degree of freedom. Motor 710 may be any suitable actuator, such as a capstan drive or a series elastic actuator. For example, to provide that force, motor 710 may comprise a capstan drive with a given P. A capstan drive motor 710 may have low torque and high angular velocity. To modify this to provide high torque and low angular velocity, a linkage 730 may be arranged between capstan drive motor 710 and a circular member 720. Linkage 730 may transition the rotation of the motor such that ten rotations of capstan drive motor 710 may result in one rotation of circular member 720. This may be referred to as a gearing ratio, and may translate the low torque of capstan drive motor 710 to an increased torque of circular member 720 with a decreased speed for the movement of a joint coupled to motor 710.

In some embodiments, in addition to linkage 730, a speed reduction mechanism, such as a gearbox or a harmonic drive may be used between motor 710 and linkage 730. This may provide additional gearing. It will be appreciated that any value of gearing ratio may be used, using any combination of linkage 730 and gearing boxes, with an understanding that an increase in angular momentum corresponds to a decrease in torque, and vice-versa, as total power (P) must remain constant. Thus, a trade-off may be experienced as higher torque are achieved through higher gearing ratios, but with a corresponding decrease in speed. Different values of motor powers and gearing ratios may be used for each of the different portions, and even for each of the joints within each of the portions. For example, shoulder portion 120 may use a capstan drive with a first power P, and use a gear box with a gearing ratio of twelve as well as a linkage with a gearing ratio of ten, totaling a gearing ratio of one-hundred and twenty. In contrast, elbow portion 130 may use a capstan drive with a lower power P than that of the capstan drive of shoulder portion, and may only use a linkage with a gearing ratio of ten.

As will be appreciated by those in the art, various sizes and types of motors may be used and still be within the scope of the present disclosure. Further, when determining the type of motor to use, it will be realized that there may be dependencies between the different portions. For example, forearm portion 140 may depend on elbow portion 130; forearm portion 140 and elbow portion 130 may depend on shoulder portion 120; and forearm portion 140, elbow portion 130, and shoulder portion 120 may depend on back portion 110.

As an illustrative example and in no way limiting, a motor of shoulder portion 120 may have the burden of moving elbow portion 130 and forearm portion 140 in addition to any other burden required to move the joint of shoulder portion 120. Thus, a person of ordinary skill in the art may desire to use lighter motors in forearm portion 140 and elbow portion 130 and be more willing to use heavier motors in shoulder portion 120 and back portion 110. This may be because the cost, including financial cost of materials, design costs (e.g. space constraints), and energy costs are increased on the joint being altered as well as on each portion from which that joint depends. For example, as the size of a motor in a dependent joint is increased, it may exponentially increase the weight of motors for joints from which the modified joint depends. For example, if the weight of forearm portion 140 is increased by using a larger motor for forearm portion 140, the motor for elbow portion 130 may need to be increased to handle the increased weight; then, the motors for shoulder portion 120 may need to be increased to account for the increase in weight of both forearm portion 140 and elbow portion 130; then, the motor(s) for back portion 110 may need to be increased to account for the increase in weight in forearm portion 140, elbow portion 130, and shoulder portion 120. Thus, the choice of motors for each of the joints in upper-body device 100 may be selected with dependencies in mind.

FIGS. 8A-8E illustrate an example of an alternative upper-body device 800, in accordance with the present disclosure. As shown in FIGS. 8A-8E, upper-body device 800 may be similar to upper-body device 100, but with some modifications. For example, an alternative upper-body device 800 may include the use of a parallelogram linkage 827 or four bar linkage as well as a fixed linkage (not shown, but similar to that shown in FIG. 6) to transfer the location of the axis of rotation of a device. For example, as shown in FIG. 5A, fifth hinge joint 127 may pivot about axis 121E, which is outside of the user's body. However, as seen in FIG. 4, the axis of rotation for clavicle 410 may be within the user's body. By using parallelogram linkage 827, the axis of rotation for the hinge joint reproducing the forward and backward motion of the clavicle may be moved from outside of the body, as shown in FIG. 5A, to inside a user's shoulder. For example, parallelogram linkage 827 may be used to provide circular travel motion for center point 824 (which may be analogous to point 147E in FIG. 6 moving along a circular trajectory with center of rotation 144). With motion of parallelogram linkage 827, center point 824 may be relocated to match the center of the ball and socket joint of a user's shoulder as the shoulder moves forward and backward and may prevent a kinematic discrepancy between the center of motion of a user's shoulder and the location of joint 127, shown in FIG. 5A.

Figure 8A:
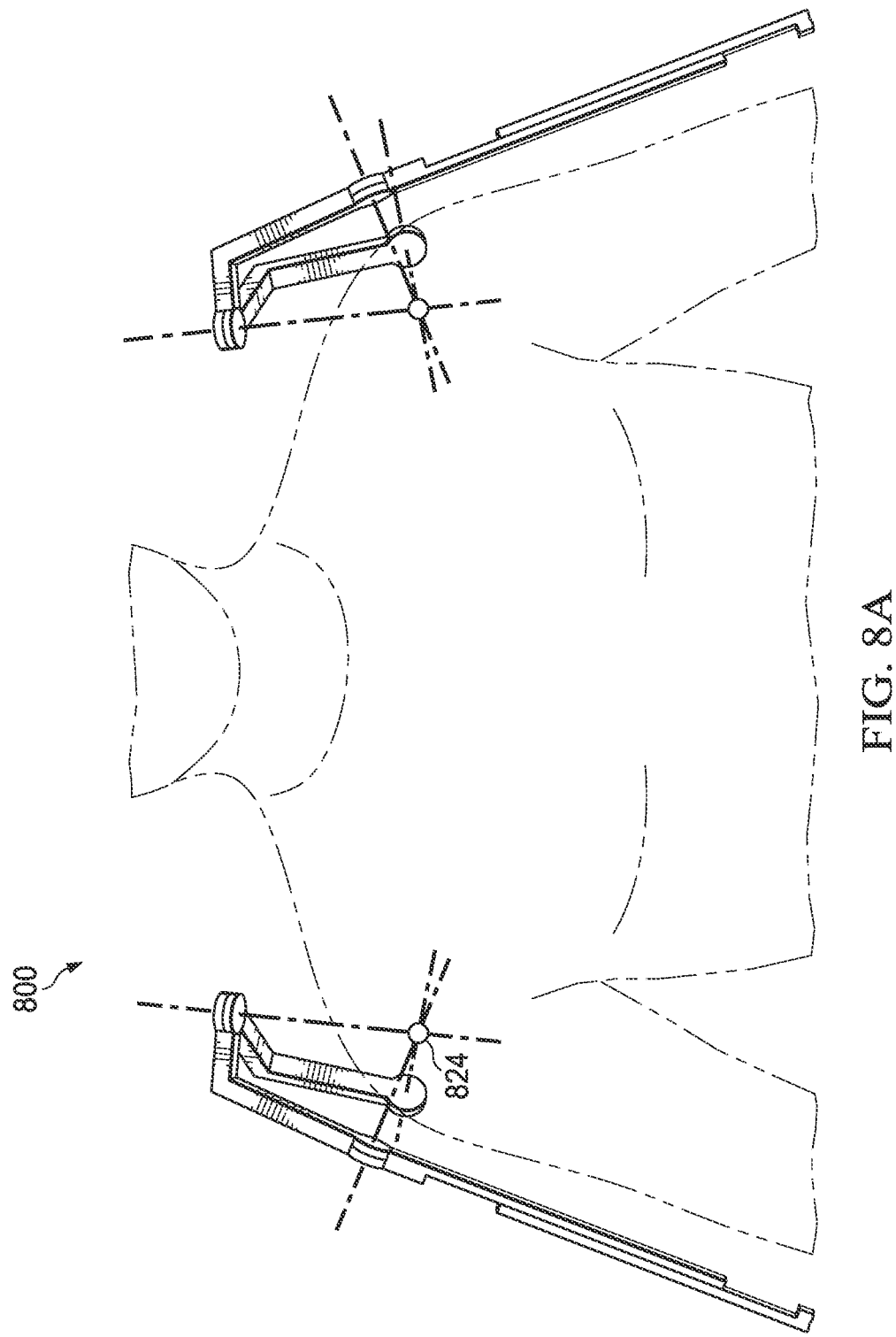
Figure 8C:
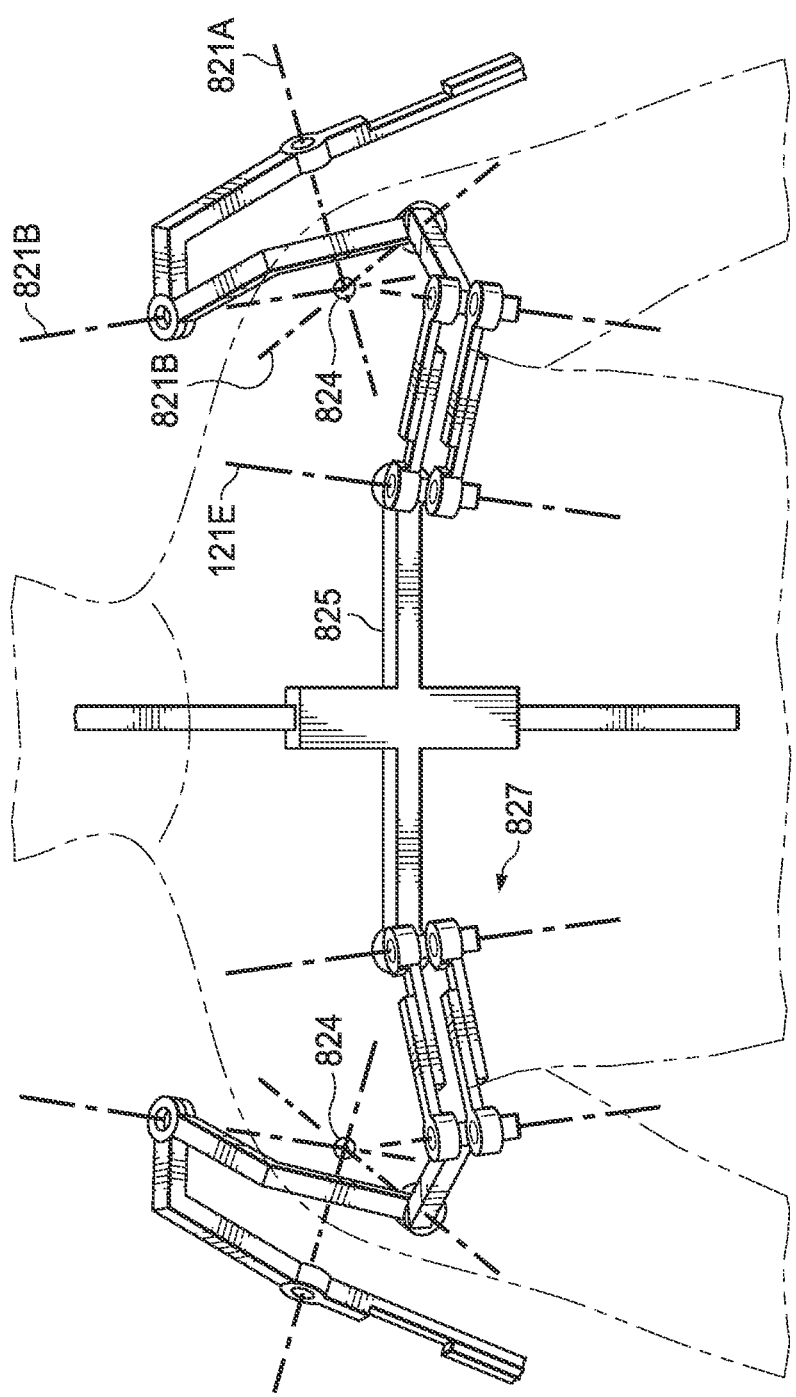
Figure 8D:
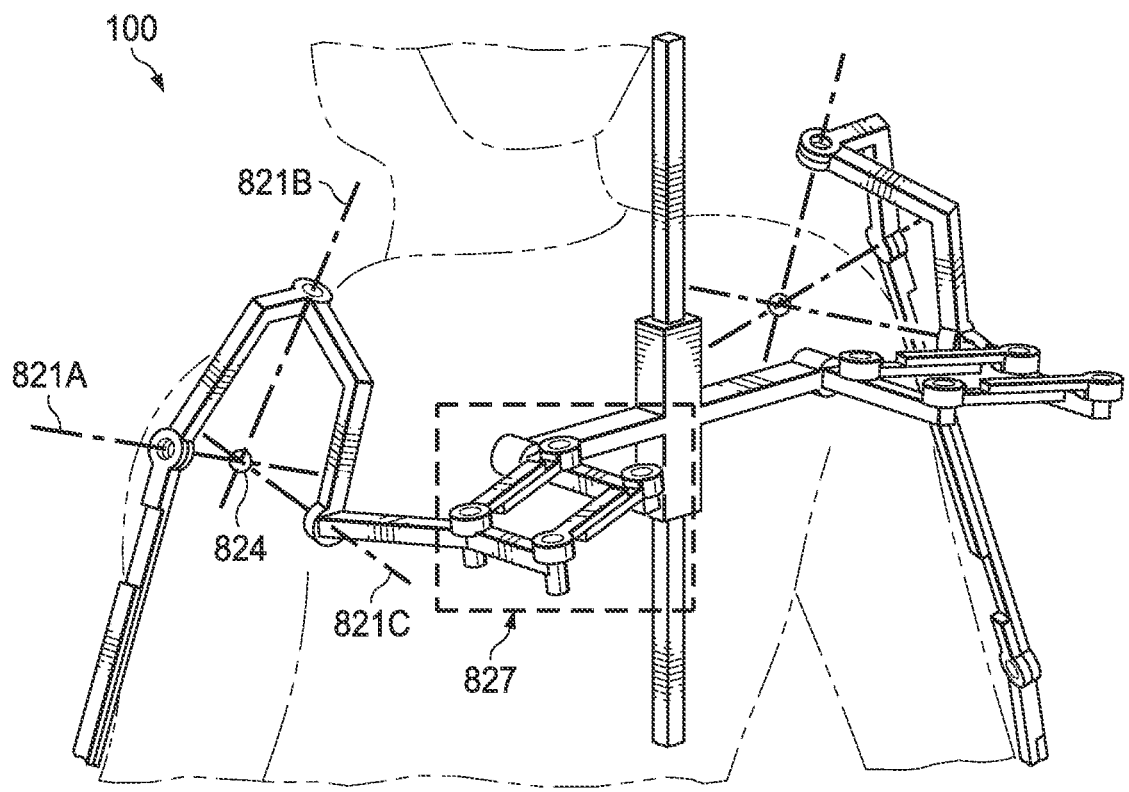
Figure 8E:
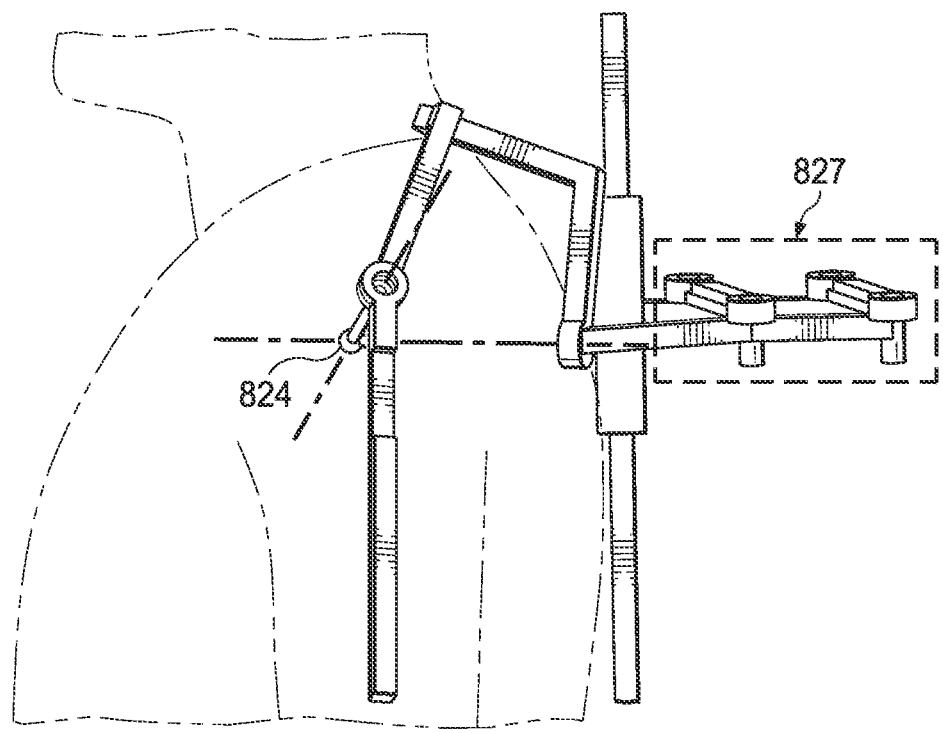

The two axes as shown in FIGS. 8B and 8C may correspond to axes 121D and 121E of FIG. 5B and may be relocated away from the center of the sternoclavicular joint to a location just outside of a user's body and having a fixed member 825 which may have an adjustable length. The length of fixed member 825 may dictate the location of the two axes shown in FIGS. 8B and 8C. This may be because the center of rotation for the circular trajectory of the center of the ball and socket joint for shoulder elevation/depression and protraction/retraction may be actually offset from the sternoclavicular joint. With reference to FIGS. 9A and 9B, this phenomena may be explained by a scenario where, as the shoulder elevates or protracts, the distance between sternoclavicular joint and the ball and socket joint may be getting closer as muscle contraction around the shoulder joint increases. Cartilage which may fill space around the sternoclavicular joint, glenohumeral joint (i.e. shoulder ball and socket joint), and acromioclavicular joint (connecter between clavicle bone and the ball socket joint) may be deformed during muscle contraction. This may cause the radius of circular movement of the ball and socket joint during shoulder elevation/depression or protraction/retraction (i.e. forward/backward) to be getting shorter as the shoulder shrugs more. This may cause the apparent center of rotation to be located outside of the sternoclavicular joint along the frontal plane.

The joints creating axes 821A, 821B, and 821C may be oriented to replicate the ball and socket joint of the shoulder prior to the addition of parallelogram linkage 827 to upper body device 800. This may allow the motion of the clavicle to be better represented, both the elevation/depression movement and the protraction/retraction movement.

Figure 10:
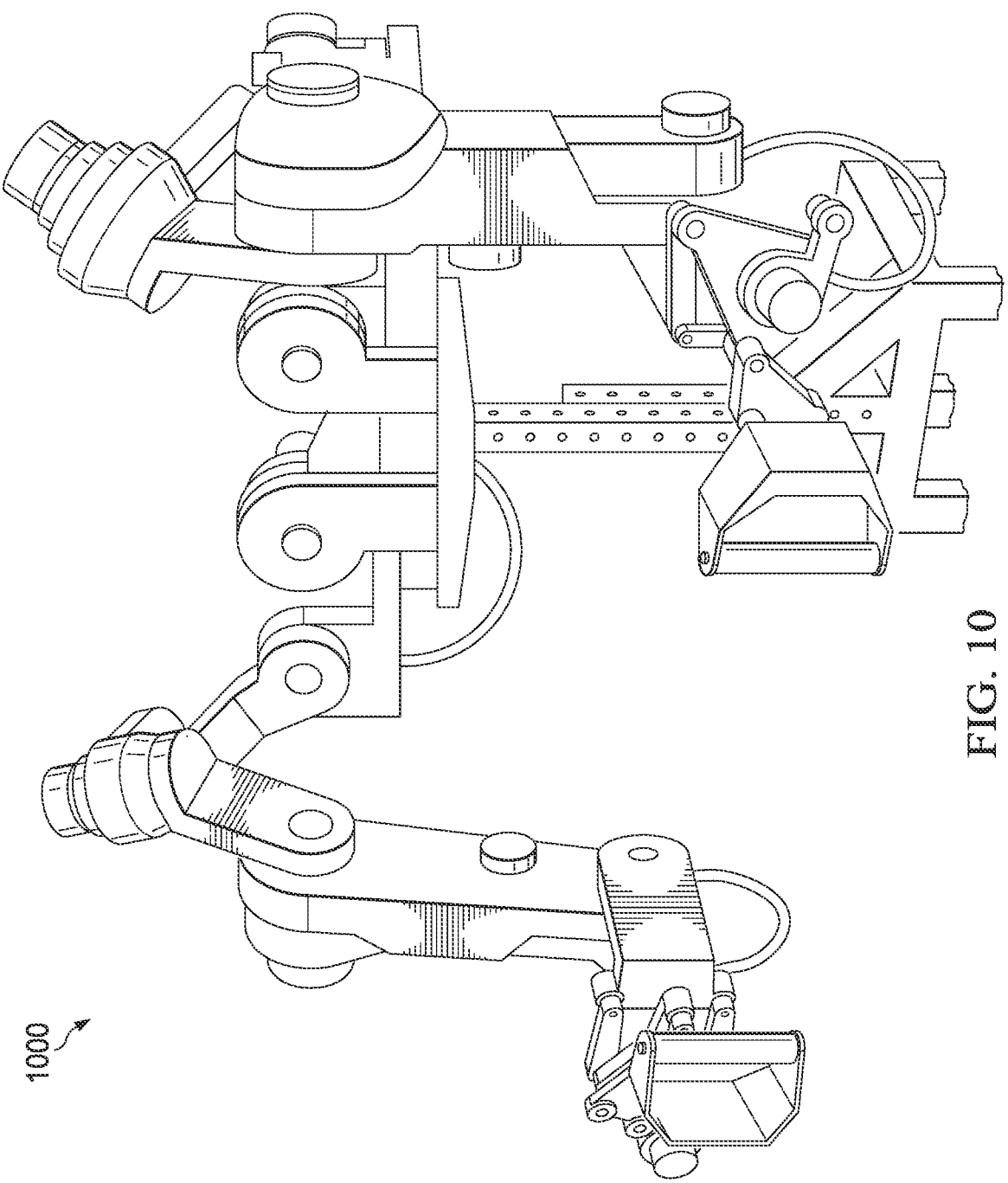
FIG. 10 illustrates an example of an upper body exoskeleton robot, in accordance with some embodiments of the present disclosure.
Figure 11:
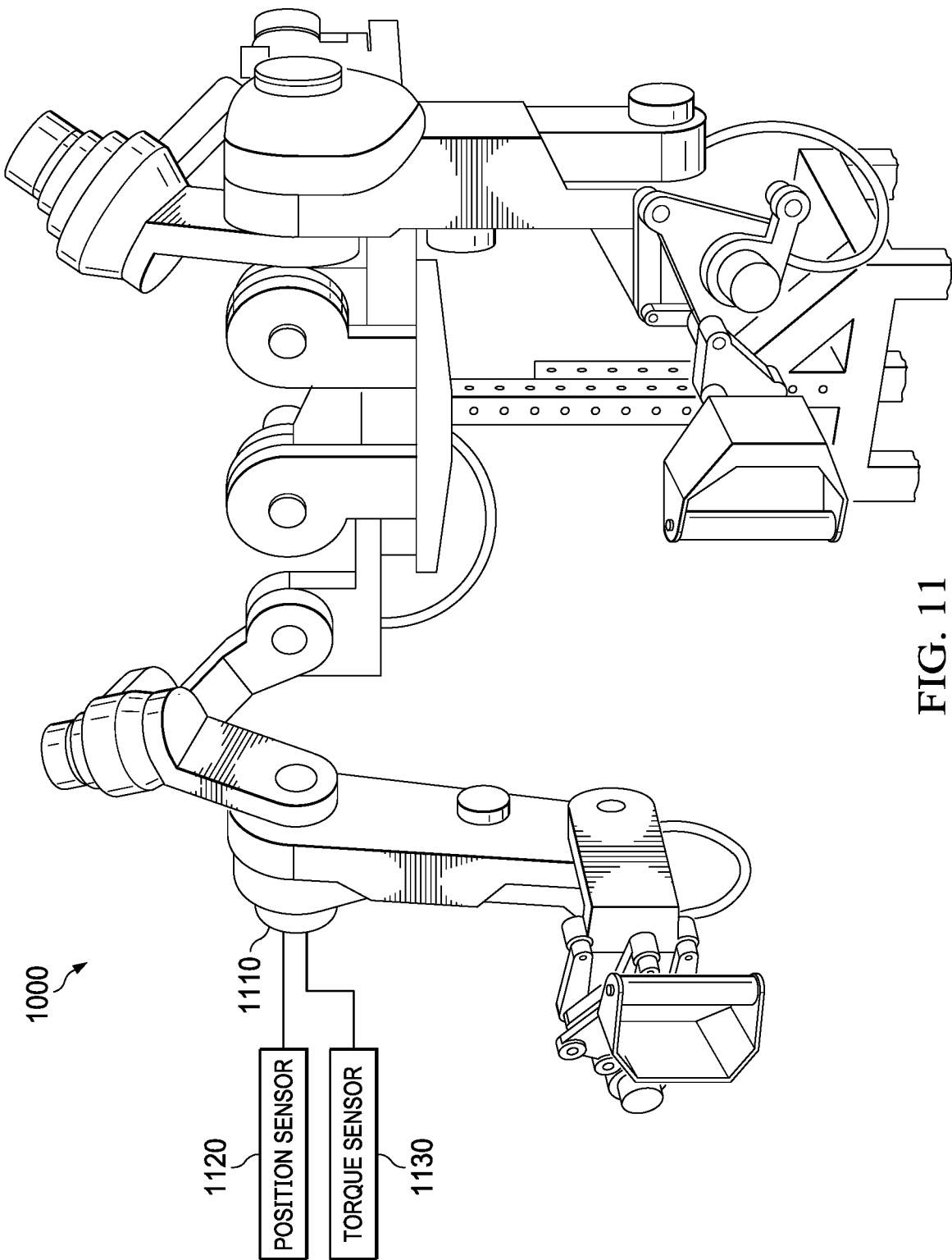
FIG. 11 illustrates an example of an upper body exoskeleton robot, including an actuator and sensors, in accordance with some embodiments of the present disclosure.

It will be appreciated that the various modifications, improvements, uses, and indications of the present disclosure with respect to upper-body device 100 are equally applicable to upper-body device 800. FIG. 10 illustrates an example of an upper body exoskeleton robot, in accordance with some embodiments of the present disclosure. Upper body exoskeleton robot 1000 includes series elastic actuators (SEAs) 1110 to operate the joints, as illustrated in FIG. 11. The SEAs may operate similar to motor 710 and linkage 730, shown in FIG. 7, and may additionally include a gear box. The output shaft of the SEA may be directly connected to the joint without having curved member 720. The SEA may include a brushless direct current (DC) motor, a harmonic drive, and a rotation spring. The SEA may additionally include one or more position sensors 1120 and torque sensors 1130 that may detect the hinge joint deflection and detect the deflection of the rotation spring to measure and control the torque of the hinge joint to which the SEA is attached. The SEAs may actuate the joints of upper body exoskeleton robot 1000 such that upper body exoskeleton robot 1000 has the capability of dedicatedly controlling force, mechanical impedance, position, and/or velocity. Upper body exoskeleton 1000 may be adjustable to accommodate users of various body sizes and may provide switches to turn off upper body exoskeleton robot 1000 in the case of an emergency.

The location of the joints on upper body exoskeleton 1000 may be adjusted to provide clearance for parts of the user's body (e.g., a user's head). The location of the joints may also be modified to prevent or minimize the occurrence of mechanical singularities. Mechanical singularities may occur when the three axes of the ball and socket joint lie in a common plane or when two axes are aligned.

While the present disclosure may describe a single joint at a time, it will be appreciated that the present disclosure envisions that all of the joints will move in cooperation, and that both sides of the body may be reproduced by the motion of upper-body device 100. For example, the motion of rowing may utilize all of the joints on both sides of the body working in coordination. In such an embodiment in which a back portion 110 includes two degrees of freedom, shoulder portions 120 each include five degrees of freedom, each elbow portion 130 includes one degree of freedom, and each forearm portion 140 includes one degree of freedom, there may be a total of sixteen degrees of freedom for upper-body device 100.

In some embodiments, upper-body device may be connected to a processing apparatus, for example, a computer with a processor, an application-specific integrated circuit (ASIC), a microcontroller, or some other electronic device. This processing device may be configured to provide instructions to upper-body device 100 regarding the actuation of the various motors of upper-body device 100. For example, it may direct when certain motors are to be engaged, to what strength, and at what speed. In addition, processing device may be configured to operate each of the various joints and portions of upper-body device such that a fluid, human-like motion is reproduced.

It will be appreciated that in addition to the mechanical structures described herein, upper-body device 100 may include some mechanism (for example wires) to carry power and/or data to the various motors of upper-body device 100. In addition, in some embodiments, upper-body device 100 may include a variety of sensors throughout upper-body device 100. This may provide feedback when a user of upper-body device exerts a force on any portion of upper-body device 100, and may further measure the magnitude of that force. For example, if a user of upper-body device 100 were to contract their bicep to raise their forearm, a sensor may measure the magnitude and location of force exerted on upper-body device 100 to accomplish this task. In addition to force sensing, there may be sensors in upper-body device 100 to recognize and measure the location of various portions of upper-body device 100. For example, if a user of upper-body device 100 were to raise their arm over their head, various sensors throughout upper-body device 100 may measure any spatial change of the sensor as the action is accomplished. Thus, in some embodiments, the mechanism for carrying data may be bi-directional, both transmitting data to various portions of upper-body device (for example, the amount of force and duration of force to be applied by a motor) as well as receiving data from various sensors and/or motors (for example, reporting the status of a motor or the triggering of an event measured by a sensor).

In some embodiments, the mechanisms for carrying data and/or wire may be connected to and/or under the control of the processing device.

The present disclosure may be used in a wide-variety of applications. For example, this device may be beneficial for stroke patients who may have lost various upper-body functions. By using this device, an exercise regime may be implemented where a patient may be able to perform exercises with a certain amount of assistance from upper-body device 100. For example, a pre-programmed exercise routine may be used, or a physical therapist may give a specific exercise routine. In some embodiments, a therapist may be the user of upper-body device in a learning mode when helping upper-body device to "learn" the exercise motions to be followed. For example, a therapist may go through a series of motions and sensors may measure locations, forces, and/or motor speeds that may be implemented to recreate that motion. Then a patient may use upper-body device 100 to go through the learned motions. In this way, a physical therapist may not need to be present as a patient exercises using upper-body device 100.

In addition to the context of medical recoveries, the same principles may be applied to general fitness equipment. For example, a user of upper-body device 100 may go through a series of exercises in which upper-body device 100 provides resistance, rather than assistance, to the user as they go through a series of motions. In this way, a user of upper-body device 100 may be given a specific exercise routine. Similarly, just as a physical therapist could go through a learning mode to teach upper-body device 100 a particular set of motions, a personal trainer could also provide a personalized set of exercises for a user of upper-body device 100.

The present disclosure may also have application in the entertainment industry. For example, video game systems may provide responsive motions to physically recreate motions or movement happening in the video game. In this way, a more interactive and engrossing video game experience may be developed.

Additionally, the present disclosure may have application for the military. For example, upper-body device 100 may provide increased strength or endurance to a solider using upper-body device 100 beyond their own physical limitations. For example, as a sensor senses a soldier moving their arms or shoulders in a certain way, upper-body device 100 may exert additional force in that same direction to lessen the effort required by the soldier. Additionally, the speed of a soldier's motions may be accelerated. For example, if a motion is sensed by the sensors of upper-body device, for example, a throwing motion, that motion may be completed at an accelerated rate by upper-body device 100. Upper-body device 100 may also allow soldiers to lift heavy loads. For example, as a soldier lifts a certain load the soldier's effort may be augmented by upper-body device also exerting additional force in the same direction the soldier may be lifting. The present disclosure may also be beneficial in any other setting in which heavy loads may need to be lifted, for example and in no way limiting, emergency response to accidents, industrial processing, or manufacturing.

In some embodiments, the present disclosure may include passive support elements (for example spring elements) to facilitate the support of various joints, framework, or other members of an upper-body device. For example, a combination of a linear spring and non-linear pulley may be used. A description of a non-circular pulley-spring mechanism and the design of such a mechanism is described in Bongsu Kim and Ashish Deshpande, *Design of Nonlinear Rotational Stiffness using a Non-circular Pulley-Spring Mechanism,*

Journal of Mechanisms and Robotics (2014), incorporated in material part by reference herein.

This disclosure encompasses all changes, substitutions, variations, alterations, and modifications to the example embodiments herein that a person having ordinary skill in the art would comprehend. Similarly, where appropriate, the appended claims encompass all changes, substitutions, variations, alterations, and modifications to the example embodiments herein that a person having ordinary skill in the art would comprehend. Moreover, reference in the appended claims to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative. For example, various embodiments may perform all, some, or none of the steps described above. Various embodiments may also perform the functions described in various orders.

Although the present disclosure has been described above in connection with several embodiments; changes, substitutions, variations, alterations, transformations, and modifications may be suggested to one skilled in the art, and it is intended that the present disclosure encompass such changes, substitutions, variations, alterations, transformations, and modifications as fall within the spirit and scope of the appended claims.

What is claimed is:

1. A robotic shoulder joint comprising:
a first hinge joint with a first axis of rotation configured to be oriented towards a center of a human shoulder joint, the first axis of rotation to be aligned with a frontal axis of a user;
a second hinge joint coupled to the first hinge joint, with a second axis of rotation oriented between 55° and 75° from the first axis of rotation and configured to be oriented towards the center of the human shoulder joint;
a third hinge joint coupled to the second hinge joint, with a third axis of rotation oriented between 55° and 75° from the second axis of rotation and oriented between 50° and 80° from the first axis of rotation, configured to be oriented towards the center of the human shoulder joint; and
a fourth hinge joint, coupled to the third hinge joint, with a fourth axis of rotation to provide an additional degree of freedom to the robotic shoulder joint.

2. The robotic shoulder joint of claim 1, wherein at least one of the first hinge joint, the second hinge joint, the third hinge joint, or the fourth hinge joint is coupled to an actuator to provide motive force to the at least one of the first hinge joint, the second hinge joint, the third hinge joint, or the fourth hinge joint.

3. The robotic shoulder joint of claim 2, wherein the actuator comprises a speed reduction mechanism to increase a torque of the at least one of the first hinge joint, the second hinge joint, the third hinge joint, or the fourth hinge joint.

4. The robotic shoulder joint of claim 2, wherein the actuator comprises at least one of a sensor to detect and control a torque of the actuator, a sensor to detect and control a position of the actuator, or combinations thereof.

5. The robotic shoulder joint of claim 2, wherein the actuator comprises at least one of a gear box, a harmonic drive, or combinations thereof to increase a torque of the at least one of the first hinge joint, the second hinge joint, the third hinge joint, or the fourth hinge joint.

6. A robotic exoskeleton comprising:
first and second shoulder portions, each of the first and second shoulder portions providing at least four degrees of freedom;
two elbow portions, each elbow portion providing at least one degree of freedom; and
two forearm portions, each forearm portion providing at least one degree of freedom;
wherein the first shoulder portion includes:
a first joint with a first axis of rotation configured to be oriented towards a center of a human shoulder joint;
a second joint, coupled to the first joint, with a second axis of rotation configured to be oriented towards the center of the human shoulder joint;
a third joint, coupled to the second joint, with a third axis of rotation configured to be oriented towards the center of the human shoulder joint;
a fourth joint, coupled to the third joint, with a fourth axis of rotation to provide a degree of freedom of the at least four degrees of freedom of the first shoulder portion to the robotic exoskeleton; and
a fifth joint with a fifth axis of rotation to provide another degree of freedom of the at least four degrees of freedom of the first shoulder portion to the robotic exoskeleton;
wherein: (a) the second axis of rotation is configured to be oriented between 55° and 75° from the first axis of rotation; and (b) the third axis of rotation is configured to be oriented between 55° and 75° from the second axis of rotation and configured to be oriented between 50° and 80° from the first axis of rotation.

7. The robotic exoskeleton of claim 6, wherein at least one of the first, second, third, or fourth joints is coupled to an actuator to provide motive force to the at least one of the first, second, third, or fourth joints.

8. The robotic exoskeleton of claim 7, wherein the actuator comprises a speed reduction mechanism to increase a torque of the at least one of the first, second, third, or fourth joints.

9. The robotic exoskeleton of claim 7, wherein the actuator comprises at least one of a sensor to detect and control a torque of the actuator, a sensor to detect and control a position of the actuator, or combinations thereof.

10. The robotic exoskeleton of claim 7, wherein the actuator comprises at least one of a gear box, a harmonic drive, or combinations thereof to increase a torque of the at least one of the first, second, third, or fourth joints.

* * * * *